US012778384B2

(12) United States Patent
Sawada et al.

(10) Patent No.: US 12,778,384 B2
(45) Date of Patent: Nov. 3, 2026

(54) MANIPULATOR SYSTEM AND MANIPULATOR OPERATION METHOD

(71) Applicant: OLYMPUS CORPORATION, Tokyo (JP)

(72) Inventors: Shota Sawada, Hachioji (JP); Kosuke Kishi, Hachioji (JP)

(73) Assignee: OLYMPUS CORPORATION, Tokyo (JP)

(*) Notice: Subject to any disclaimer, the term of this patent is extended or adjusted under 35 U.S.C. 154(b) by 399 days.

(21) Appl. No.: 18/243,394

(22) Filed: Sep. 7, 2023

(65) Prior Publication Data

US 2023/0414078 A1 Dec. 28, 2023

Related U.S. Application Data

(63) Continuation of application No. PCT/JP2021/010504, filed on Mar. 16, 2021.

(51) Int. Cl.
*A61B 1/005* (2006.01)
*A61B 1/00* (2006.01)

(52) U.S. Cl.
CPC ...... *A61B 1/00057* (2013.01); *A61B 1/00006* (2013.01); *A61B 1/0016* (2013.01); *A61B 1/0052* (2013.01); *A61B 1/0057* (2013.01); *A61B 1/009* (2022.02)

(58) Field of Classification Search
CPC .............. A61B 1/0052; A61B 1/00057; A61B 1/00006; A61B 1/0057; A61B 1/0016; A61B 1/000096; A61B 1/00062; A61B 1/009; B25J 9/1692; B25J 3/00
See application file for complete search history.

(56) References Cited

U.S. PATENT DOCUMENTS

2009/0287054 A1* 11/2009 Dejima ................ A61B 1/0052 600/146
2011/0245844 A1 10/2011 Jinno
2011/0295063 A1* 12/2011 Umemoto ............ A61B 1/0057 600/109

(Continued)

FOREIGN PATENT DOCUMENTS

EP 2 462 858 A1 6/2012
EP 3 061 418 A1 8/2016

(Continued)

OTHER PUBLICATIONS

International Search Report dated Jun. 8, 2021 received in PCT/JP2021/010504 .

*Primary Examiner* — Michael J Carey
*Assistant Examiner* — Olivia Grace Starkey
(74) *Attorney, Agent, or Firm* — Scully, Scott, Murphy & Presser, P.C.

(57) ABSTRACT

A manipulator system includes: a manipulator including a bending portion and a bending wire configured to bend the bending portion; a driving portion configured to pull and loosen the bending wire; and a control device configured to control the driving portion, wherein the control device controls the driving portion to perform an initialization operation that alternately repeats pulling and loosening of the bending wire so that an amount of change in a bending shape of the bending portion compared to when the initialization operation is started falls within a predetermined range.

17 Claims, 25 Drawing Sheets

(56) References Cited

U.S. PATENT DOCUMENTS

| | | | | |
|---|---|---|---|---|
| 2015/0105615 | A1* | 4/2015 | Kato | A61B 5/6852 600/249 |
| 2018/0092517 | A1* | 4/2018 | Graetzel | A61B 1/0051 |
| 2019/0380617 | A1* | 12/2019 | Oosake | A61B 5/1032 |
| 2020/0074655 | A1* | 3/2020 | Sakamoto | G06T 7/579 |

FOREIGN PATENT DOCUMENTS

| | | | | |
|---|---|---|---|---|
| EP | 3 097 884 | A1 | 11/2016 | |
| EP | 3 108 844 | A1 | 12/2016 | |
| EP | 3 109 013 | A1 | 12/2016 | |
| JP | 2011-206312 | A | 10/2011 | |
| JP | 2015-080845 | A | 4/2015 | |
| JP | 2015-136526 | A | 7/2015 | |
| JP | 2015-156906 | A | 9/2015 | |
| JP | 2015-157326 | A | 9/2015 | |
| JP | 6278747 | B2 | 2/2018 | |
| WO | 2011/108161 | A1 | 9/2011 | |
| WO | WO-2019155617 | A1 * | 8/2019 | A61B 1/000096 |

* cited by examiner

MANIPULATOR SYSTEM AND MANIPULATOR OPERATION METHOD

CROSS-REFERENCE TO RELATED APPLICATIONS

The present application is a continuation application based on PCT Patent Application No. PCT/JP2021/010504, filed on Mar. 16, 2021, the entire content of which is hereby incorporated by reference.

BACKGROUND

Technical Field

The present invention relates to a manipulator system and a manipulator operation method.

Description of the Background

Conventionally, a manipulator system equipped with an endoscope has been used for observation and treatment inside a hollow organ such as a digestive tract. The manipulator system includes a bending portion that can be driven to bend at an insertion portion inserted within the hollow organ. A user can operate the bending portion from an operation portion arranged outside the body.

Japanese Patent (Granted) Publication No. 6278747 (hereinafter referred to as Patent Document 1) describes a manipulator system that includes a bending portion that can be driven to bend in the insertion portion. The manipulator system described in Patent Document 1 can perform calibration for accurately driving the bending portion.

However, the manipulator system described in Patent Document 1 needs to restrain the movement of the movable part of the bending portion in order to perform calibration. Calibration is performed in a state in which the bending portion is constrained and changed into a predetermined bending shape. Calibration cannot be performed in a state where the bending portion has changed into a bending shape other than the predetermined bending shape. Calibration cannot be performed in a situation such as when the manipulator is inserted into the lumen, in which the movable portion of the bending portion cannot be constrained.

SUMMARY

The present invention provides a manipulator system that can accurately drive a bending portion by optimizing a power transmission system that transmits power for bending the bending portion regardless of a bending shape of the bending portion and whether or not a movable portion is constrained.

A manipulator system according to a first aspect of the present invention includes: a manipulator including a bending portion and a bending wire configured to bend the bending portion; a driving portion configured to pull and loosen the bending wire; and a control device configured to control the driving portion, wherein the control device controls the driving portion to perform an initialization operation that alternately repeats pulling and loosening of the bending wire so that an amount of change in a bending shape of the bending portion compared to when the initialization operation is started falls within a predetermined range.

According to the manipulator system of the present invention, regardless of the bending shape of the bending portion, the power transmission system that transmits the power for bending the bending portion can be optimized to accurately drive the bending portion.

EMBODIMENTS

First Embodiment

Figure 1:
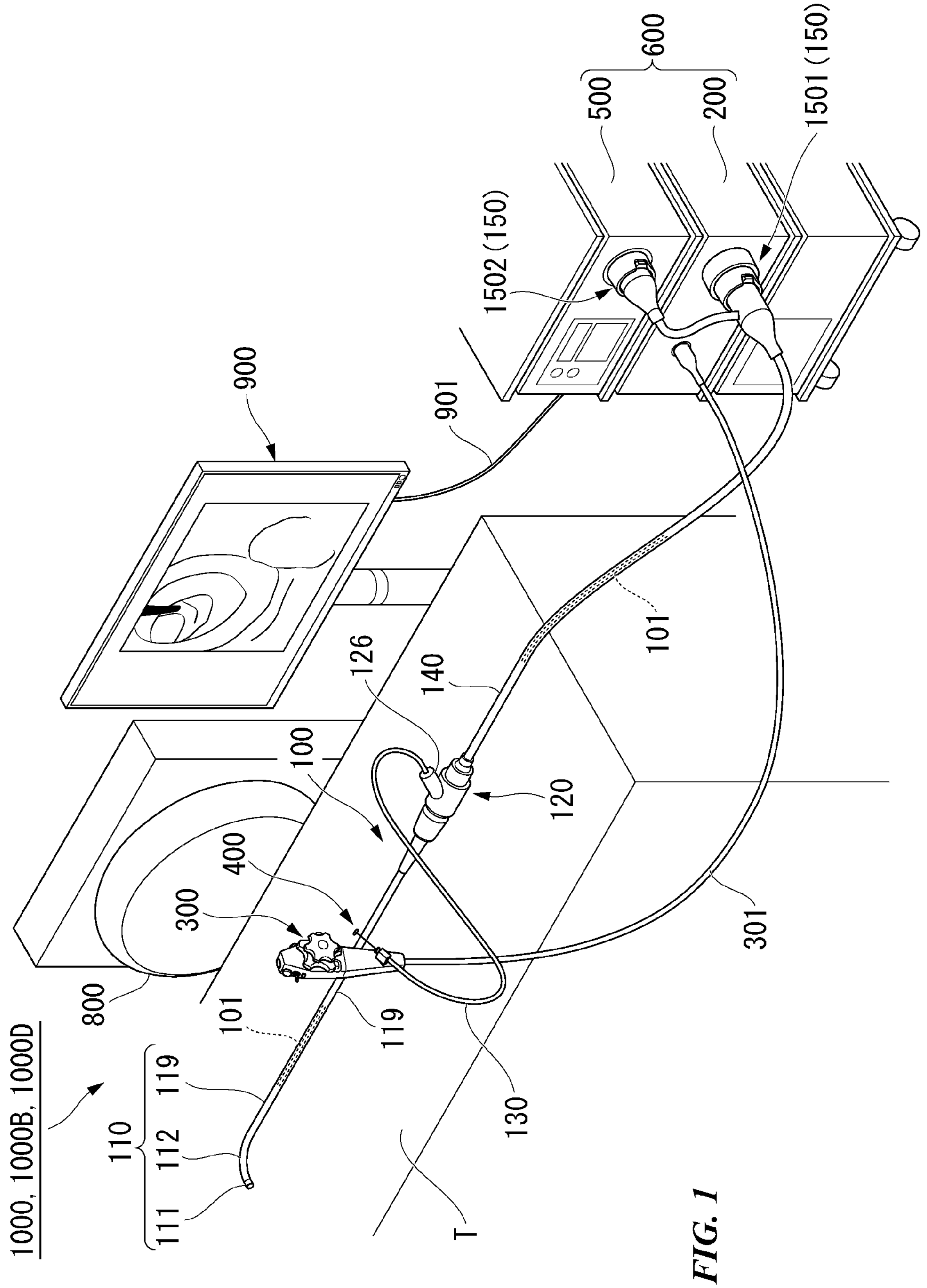
FIG. 1 is an overall view of an electric endoscope system according to a first embodiment.

An electric endoscope system 1000 according to a first embodiment of the present invention will be described with reference to FIGS. 1 to 19. FIG. 1 is an overall view of the electric endoscope system 1000 according to this embodiment. The electric endoscope system 1000 is an example of a manipulator system.

[Electric Endoscope System 1000]

The electric endoscope system 1000 is a medical system used to observe and treat the inside of a patient P lying on an operation table T, as shown in FIG. 1. The electric endoscope system 1000 includes an endoscope 10, a drive device 200, an operation device 300, a treatment tool 400, an image control device 500, an observation device 800, and a display device 900.

The endoscope 100 is a device that is inserted into the lumen of the patient P to observe and treat the affected area. The endoscope 100 is detachable from the drive device 200. An internal path 101 is formed inside the endoscope 100. In the following description, in the endoscope 100, the side inserted into the lumen of the patient P is referred to as a “distal end side (A1)”, and the side attached to the drive device 200 is referred to as a “proximal end side (A2)”.

The drive device 200 is detachably connected to the endoscope 100 and the operation device 300. The drive device 200 electrically drives the endoscope 100 by driving a built-in motor based on an operation input to the operation device 300. The drive device 200 drives a built-in pump or the like based on an operation input to the operation device 300 to cause the endoscope 100 to perform air supply and suction.

The operation device 300 is detachably connected to the drive device 200 via an operation cable 301. The operation device 300 may be capable of communicating with the drive device 200 by wireless communication instead of wired communication. A surgeon S can electrically drive the endoscope 100 by operating the operation device 300.

The treatment tool 400 is a device that is inserted through the internal path 101 of the endoscope 100 and inserted into the lumen of the patient P to treat the affected area. In FIG. 1, the treatment tool 400 is inserted into the internal path 101 of the endoscope 100 via an extension channel tube 130. The treatment tool 400 may be inserted directly into the internal path 101 of the endoscope 100 from a forceps port 126 without passing through the extension channel tube 130.

The image control device 500 is detachably connected to the endoscope 100 and acquires captured images from the endoscope 100. The image control device 500 causes the display device 900 to display captured images acquired from the endoscope 100 and GUI images and CG images for the purpose of providing information to the surgeon.

The drive device 200 and the image control device 500 constitute a control device 600 that controls the electric endoscope system 1000. The control device 600 may further include peripherals such as a video printer. The drive device 200 and the video control device 500 may be an integrated device.

The display device 900 is a device capable of displaying images such as an LCD. The display device 900 is connected to the video control device 500 via a display cable 901.

Figure 2:
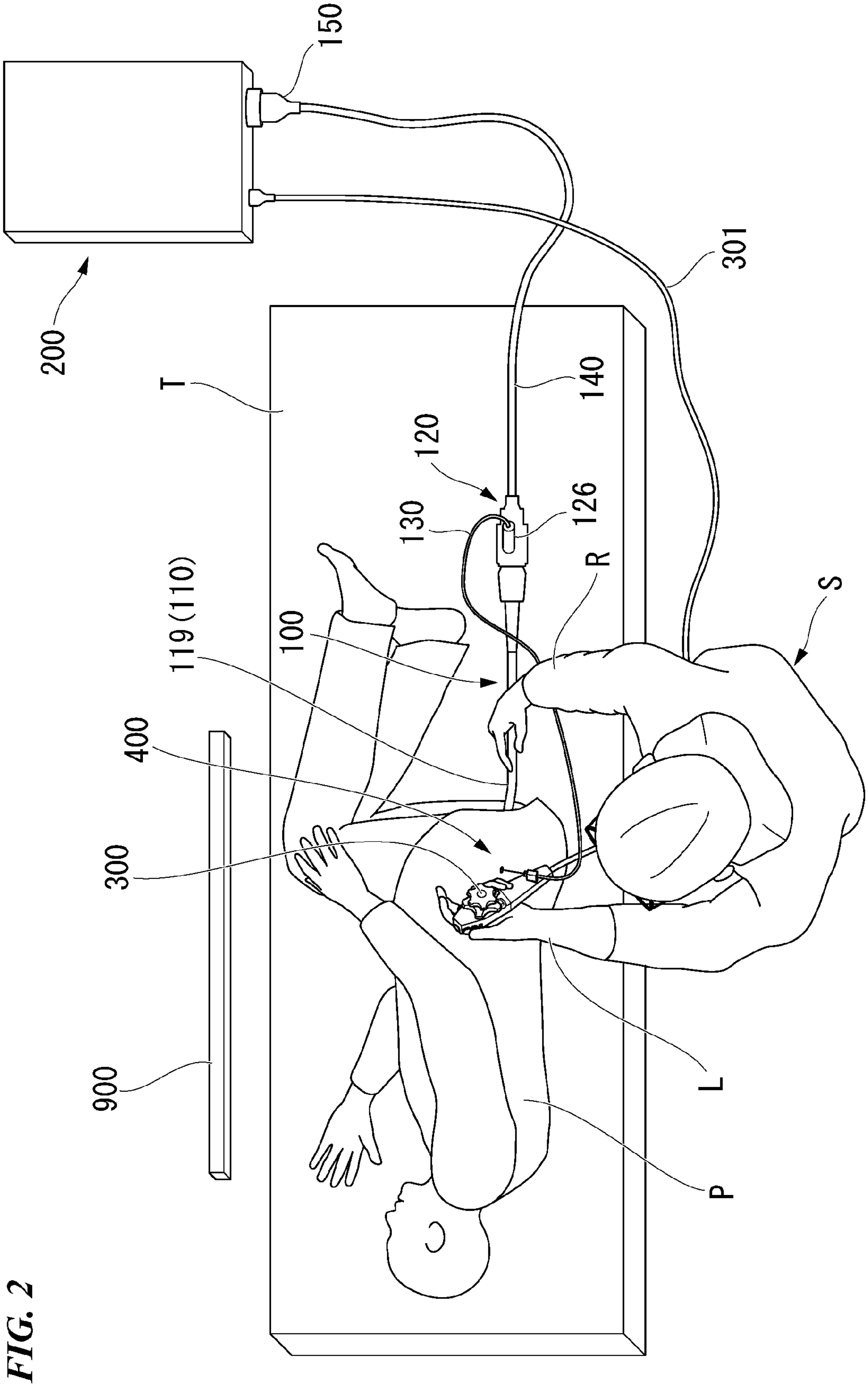
FIG. 2 is a diagram showing an endoscope and an operation device of the electric endoscope system used by a surgeon.

FIG. 2 is a diagram showing the endoscope 100 and the operation device 300 used by the surgeon S.

For example, while observing the captured image displayed on the display device 900, the surgeon S operates the operation device 300 with the left hand L while operating the endoscope 100 inserted into the lumen from the anus of the patient P with the right hand R. Since the endoscope 100 and the operation device 300 are separated, the surgeon S can operate the endoscope 100 and the operation device 300 independently without being affected by each other.

[Endoscope 100]

Figure 6:
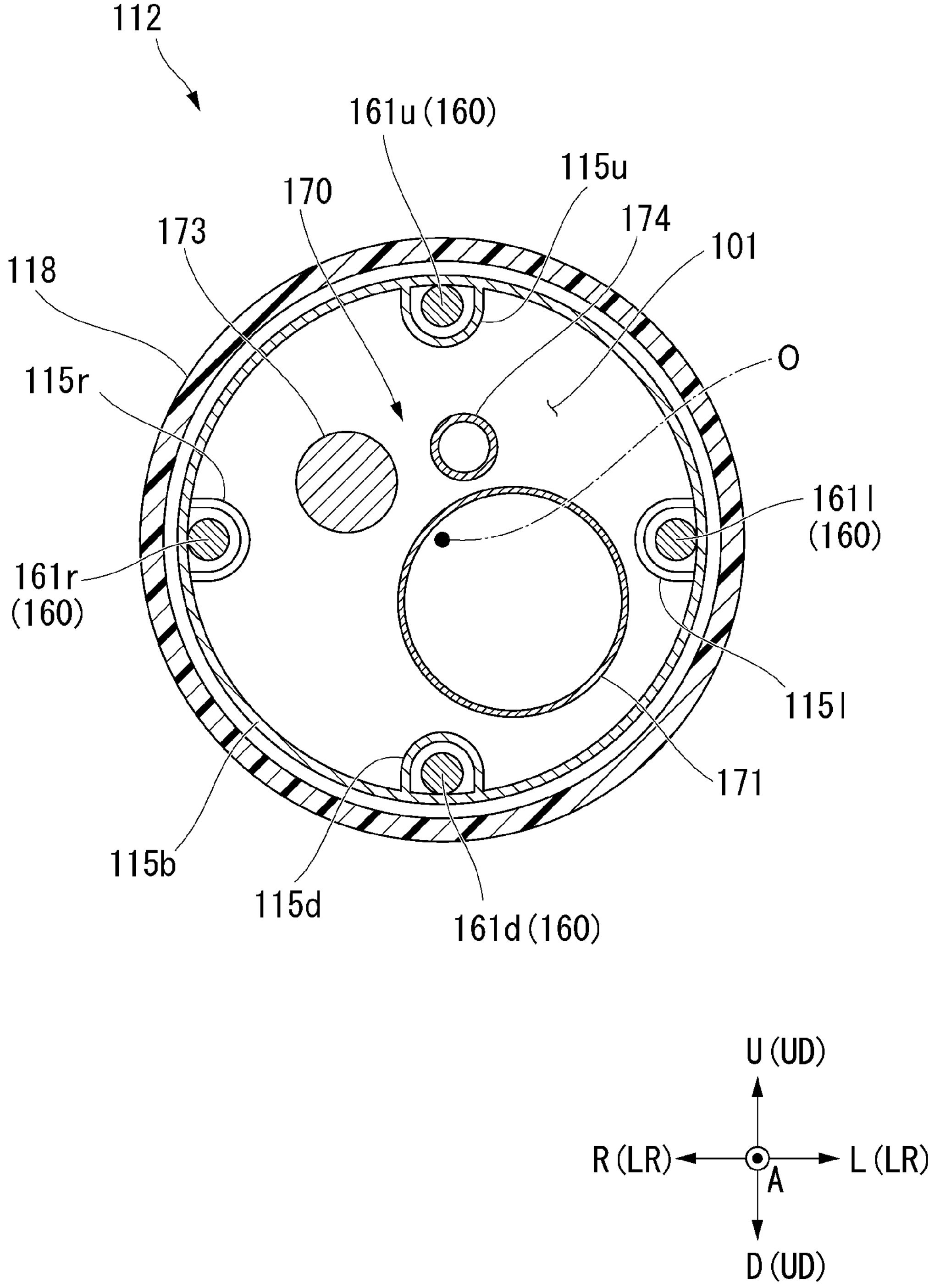
FIG. 6 is a cross-sectional view of the bending portion along line C1-C1 in FIGS. 4 and 5.

As shown in FIG. 1, the endoscope 100 includes an insertion portion 110, a connecting portion 120, an extracorporeal flexible portion 140, an attachment/detachment portion 150, a bending wire 160 (see FIG. 6), and an internal object 170 (see FIG. 6). The insertion portion 110, the connecting portion 120, the extracorporeal flexible portion 140, and the attachment/detachment portion 150 are connected in order from the distal end side. The connecting portion 120 can connect the extension channel tube 130.

Figure 3:
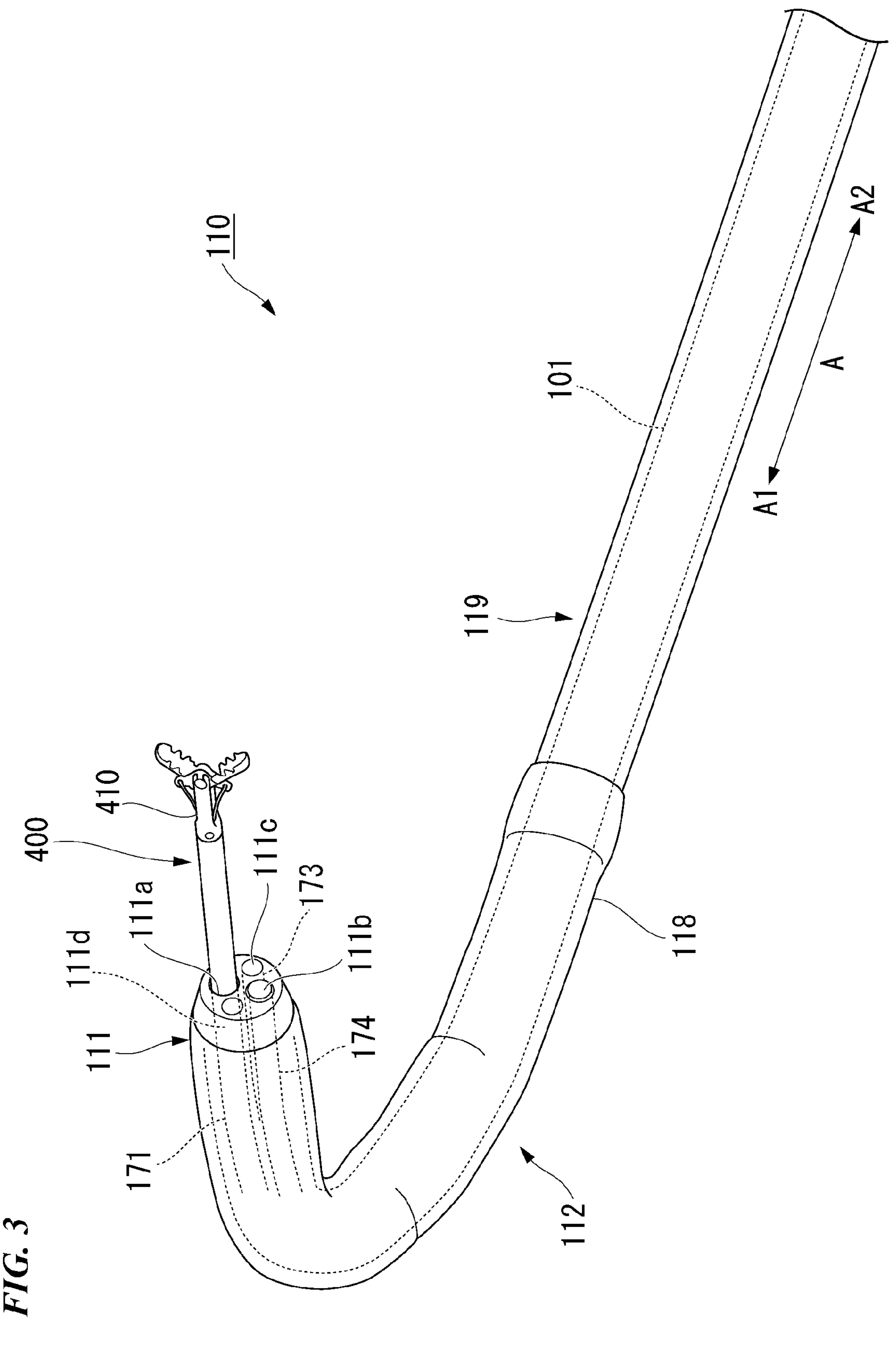
FIG. 3 is a diagram showing an insertion portion of the endoscope.

FIG. 3 is a diagram showing the insertion portion 110 of the endoscope 100.

The internal path 101 extending along the longitudinal direction A of the endoscope 100 from the distal end of the insertion portion 110 to the proximal end of the attachment/detachment portion 150 is formed inside the endoscope 100. The bending wire 160 and the internal object 170 are inserted into the internal path 101.

The internal object 170 has a channel tube 171, an air supply/suction tube 172 (see FIG. 10), an imaging cable 173, and a light guide 174.

[Insertion Portion 110]

The insertion portion 110 is an elongated long member that can be inserted into a lumen. The insertion portion 110 has a distal end portion 111, a bending portion 112 and an internal flexible portion 119. The distal end portion 111, the bending portion 112, and the internal flexible portion 119 are connected in order from the distal end side.

A magnetic coil (not shown) is built in the insertion portion 110 along the longitudinal direction A. The magnetic coil is spirally attached along the inner peripheral surface of the internal path 101 of the insertion portion 110, for example.

As shown in FIG. 3, the distal end portion 111 has an opening portion 111*a*, an illumination portion 111*b*, and an imaging portion 111*c*. The opening portion 111*a* is an opening that communicates with the channel tube 171. As shown in FIG. 3, a treatment portion 410 such as grasping forceps provided at the distal end of the treatment tool 400 through which the channel tube 171 is inserted protrudes from the opening portion 111*a*. A treatment tool sensor 111*d* that detects the treatment tool 400 is provided in the opening portion 111*a*.

The illumination portion 111*b* is connected to a light guide 174 that guides illumination light, and emits illumination light that illuminates the imaging target. The imaging portion 111*c* includes an imaging element such as a CMOS, and images an object to be imaged. The imaging signal is sent to the video control device 500 via the imaging cable 173.

Figure 4:
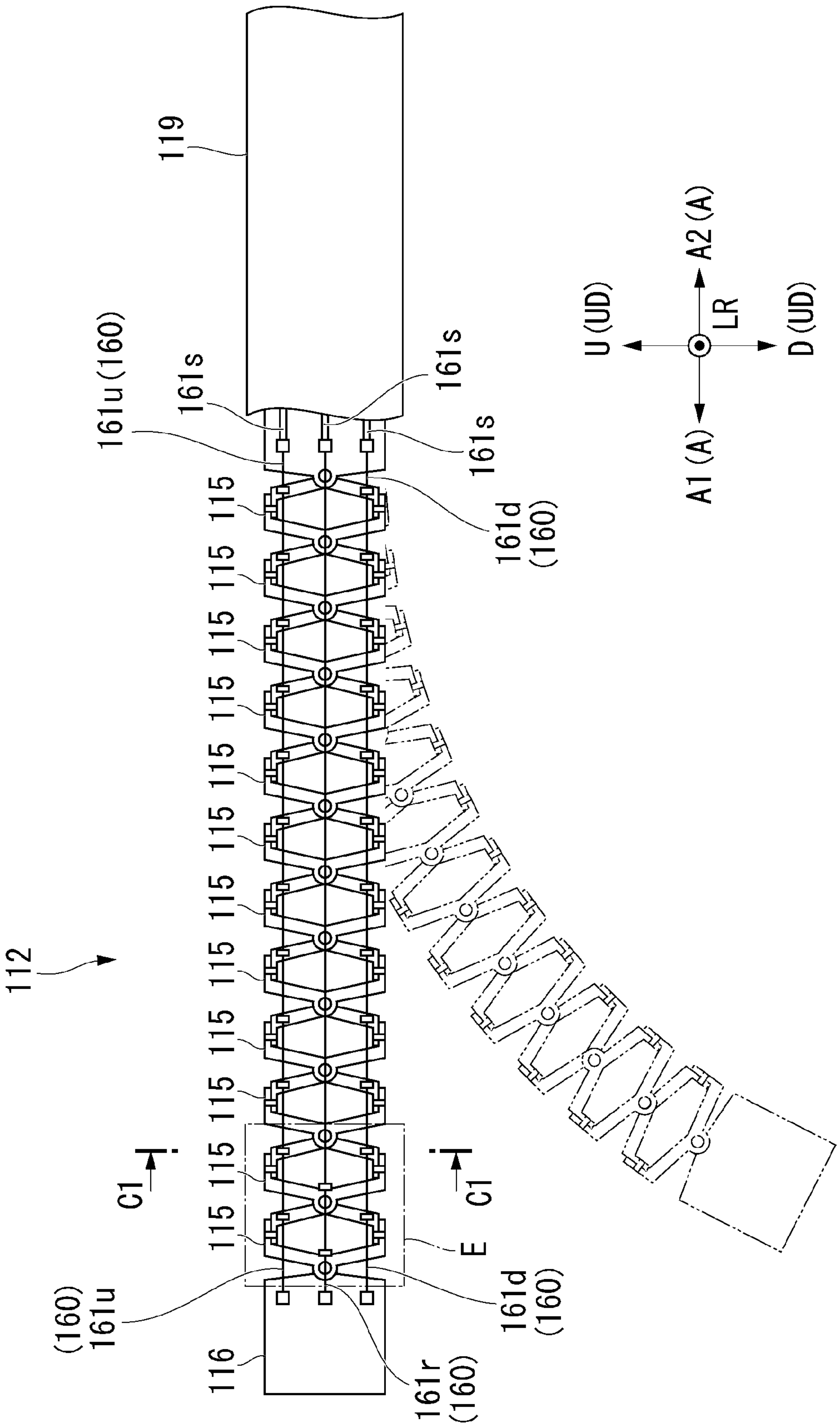
FIG. 4 is a cross-sectional view showing a part of the bending portion of the endoscope.

FIG. 4 is a diagram showing a part of the bending portion 112 as a cross-sectional view.

The bending portion 112 has a plurality of node rings (also referred to as bending pieces) 115, a distal end portion 116 connected to the distal ends of the plurality of node rings 115, and an outer sheath 118 (see FIG. 3). The plurality of node rings 115 and the distal end portion 116 are connected in the longitudinal direction A inside the outer sheath 118. The shape and number of the node rings 115 included in the bending portion 112 are not limited to the shape and number of the node rings 115 shown in FIG. 4.

Figure 5:
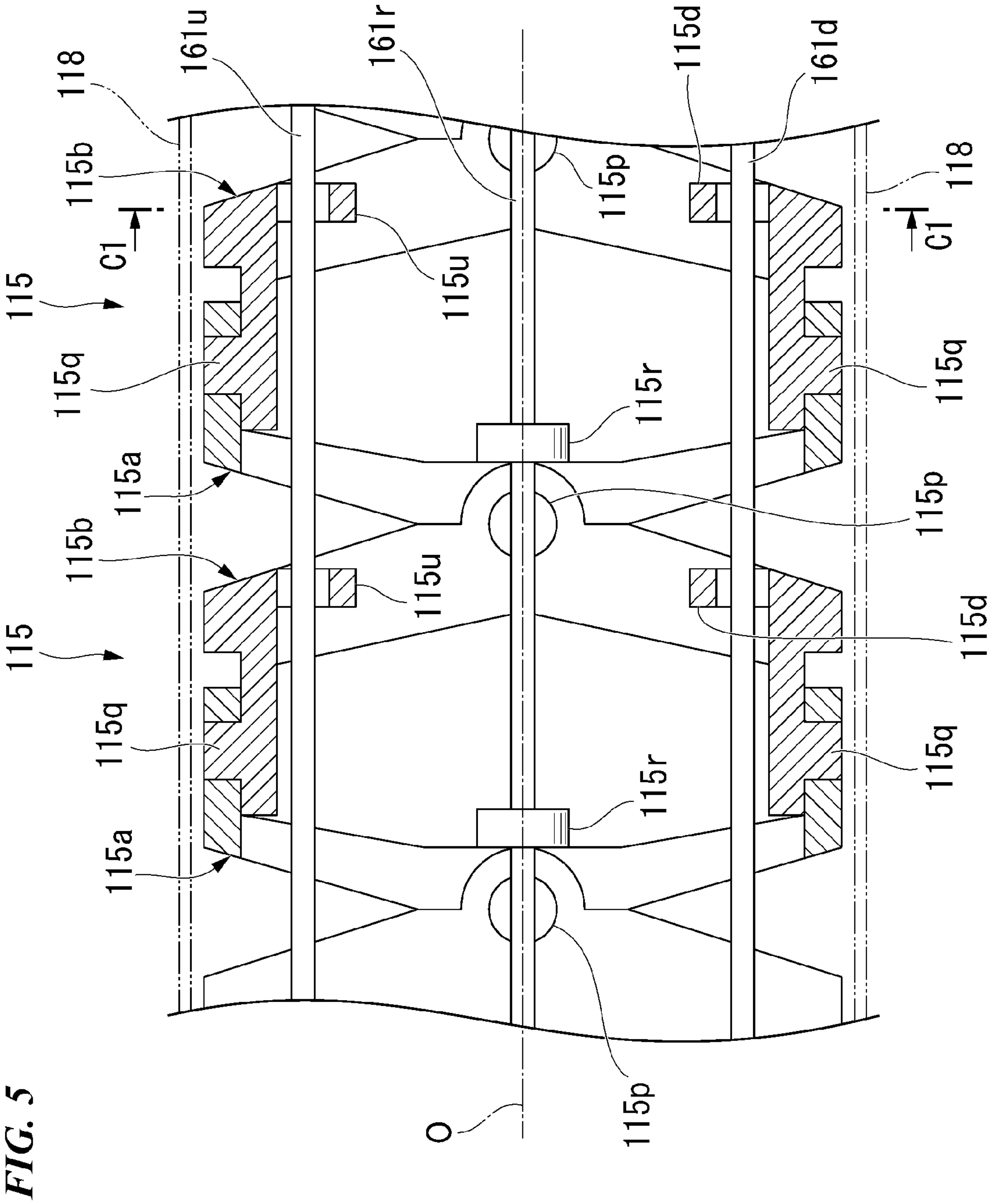
FIG. 5 is an enlarged view of a node ring of the bending portion in region E shown in FIG. 4.

FIG. 5 is an enlarged view of the node ring 115 in region E shown in FIG. 4.

The node ring 115 is a short cylindrical member made of metal. The plurality of node rings 115 are connected so that the internal spaces of adjacent node rings 115 are continuous spaces.

The node ring 115 has a first node ring 115*a* on the distal end side and a second node ring 115*b* on the proximal end side. The first node ring 115*a* and the second node ring 115*b* are connected by a first turning pin 115*p* so as to be rotatable in the vertical direction (also referred to as "UD direction") perpendicular to the longitudinal direction A.

In the neighboring node rings 115, the second node ring 15*b* of the node ring 115 on the distal end side and the first node ring 115*a* of the node ring 115 on the proximal end side are coupled to be rotatable in the vertical direction (also referred to as the "LR direction") perpendicular to the longitudinal direction A and the UD direction by a second pivot pin 115*q*.

The first node ring 115*a* and the second node ring 115*b* are alternately connected by the first turning pin 115*p* and the second pivot pin 115*q*, and the bending portion 112 can be bent in a desired direction.

FIG. 6 is a cross-sectional view of the bending portion 112 taken along line C1-C1 in FIGS. 4 and 5.

An upper wire guide 115*u* and a lower wire guide 115*d* are formed on the inner peripheral surface of the second node ring 115*b*. The upper wire guide 115*u* and the lower wire guide 115*d* are arranged on both sides in the UD direction with the central axis O in the longitudinal direction A interposed therebetween. A left wire guide 1151 and a right wire guide 115*r* are formed on the inner peripheral surface of the first node ring 115*a*. The left wire guide 1151 and the right wire guide 115*r* are arranged on both sides in the LR direction with the central axis O in the longitudinal direction A interposed therebetween.

Through-holes through which the bending wire 160 is inserted are formed along the longitudinal direction Ain the upper wire guide 115*u*, the lower wire guide 115*d*, the left wire guide 1151, and the right wire guide 115*r*.

The bending wire 160 is a wire that bends the bending portion 112. The bending wire 160 extends through the internal path 101 to the attachment/detachment portion 150. As shown in FIGS. 4 and 6, the bending wire 160 has an upper bending wire 161*u*, a lower bending wire 161*d*, a left bending wire 161*l*, a right bending wire 161*r*, and four wire sheaths 161*s*.

As shown in FIG. 4, the upper bending wire 161*u*, the lower bending wire 161*d*, the left bending wire 161*l*, and the right bending wire 161*r* are each inserted through the wire sheath 161*s*. A distal end of the wire sheath 161*s* is attached to the node ring 115 at the proximal end of the bending portion 112. The wire sheath 161*s* extends to the attachment/detachment portion 150.

The upper bending wire 161*u* and the lower bending wire 161*d* are wires for bending the bending portion 112 in the UD direction. The upper bending wire 161*u* passes through the upper wire guide 115*u*. The lower bending wire 161*d* is inserted through the lower wire guide 115*d*.

The tips of the upper bending wire 161*u* and the lower bending wire 161*d* are fixed to the distal end portion 116 of the bending portion 112, as shown in FIG. 4. The tips of the upper bending wire 161*u* and the lower bending wire 161*d* fixed to the distal end portion 116 are arranged on both sides in the UD direction with the central axis O in the longitudinal direction A interposed therebetween.

The left bending wire 161*l* and the right bending wire 161*r* are wires for bending the bending portion 112 in the LR direction. The left bending wire 161*l* passes through the left wire guide 1151. The right bending wire 161*r* passes through the right wire guide 115*r*.

The distal ends of the left bending wire 161*l* and the right bending wire 161*r* are fixed to the distal end portion 116 of the bending portion 112, as shown in FIG. 4. The tips of the left bending wire 161*l* and the right bending wire 161*r* fixed to the distal end portion 116 are arranged on both sides in the LR direction with the central axis O in the longitudinal direction A interposed therebetween.

The bending portion 112 can be bent in a desired direction by pulling or loosening the bending wires 160 (the upper bending wire 161*u*, the lower bending wire 161*d*, the left bending wire 161*l*, and the right bending wire 161*r*).

As shown in FIG. 6, the bending wire 160, the channel tube 171, the imaging cable 173, and the light guide 174 are inserted through the internal path 101 formed inside the bending portion 112.

The internal flexible portion 119 is an elongated flexible tubular member. The bending wire 160, the channel tube 171, the imaging cable 173, and the light guide 174 are inserted through the internal path 101 formed in the internal flexible portion 119.

[Connecting Portion 120]

The connecting portion 120 is a member that connects the internal flexible portion 119 and the extracorporeal flexible portion 140 of the insertion portion 110, as shown in FIG. 1. The connecting portion 120 includes a forceps opening 126 that is an insertion opening into which the treatment tool 400 is inserted.

[Extracorporeal Flexible Portion 140]

The extracorporeal flexible portion 140 is a long tubular member. The bending wire 160, the imaging cable 173, the light guide 174, and the air supply/suction tube 172 (see FIG. 10) are inserted through the internal path 101 formed inside the extracorporeal flexible portion 140.

[Attachment/Detachment Portion 150]

The attachment/detachment portion 150 includes a first attachment/detachment portion 1501 attached to the drive device 200 and a second attachment/detachment portion 1502 attached to the video control device 500, as shown in FIG. 1. The first attachment/detachment portion 1501 and the second attachment/detachment portion 1502 may be an integral attachment/detachment portion.

The internal path 101 formed inside the extracorporeal flexible portion 140 branches into the first attachment/detachment portion 1501 and the second attachment/detachment portion 1502. The bending wire 160 and the air supply/suction tube 172 are inserted through the first attachment/detachment portion 1501. The imaging cable 173 and the light guide 174 are inserted through the second attachment/detachment portion 1502.

Figure 7:
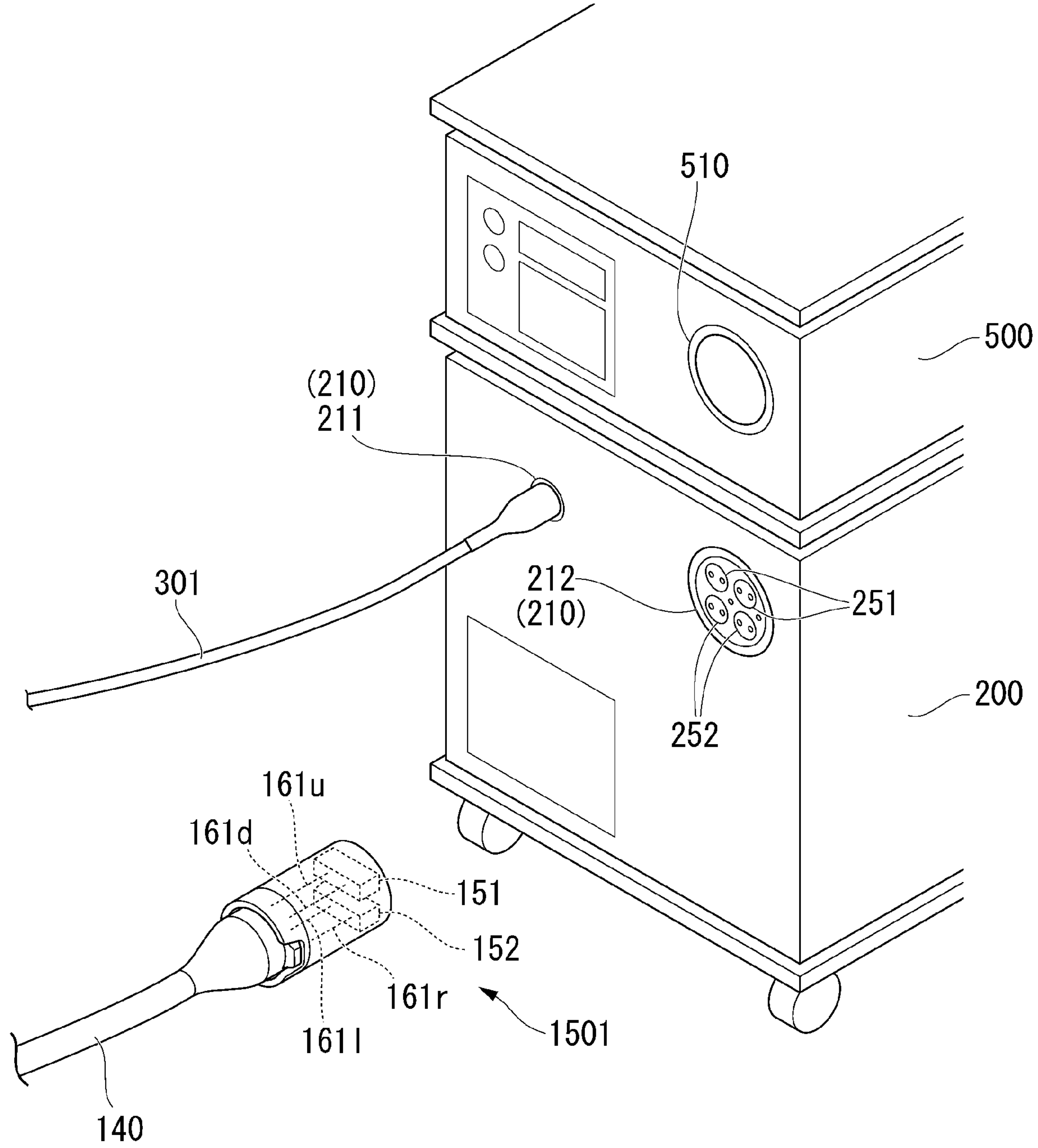
FIG. 7 is a diagram showing a first attachment/detachment portion before attachment to the drive device of the electric endoscope system.

FIG. 7 is a diagram showing the first attachment/detachment portion 1501 before being attached to the drive device 200.

The first attachment/detachment portion 1501 has a vertical bending wire attachment/detachment portion 151 and a horizontal bending wire attachment/detachment portion 152.

The vertical bending wire attachment/detachment portion 151 is a mechanism that detachably connects wires (the upper bending wire 161*u* and the lower bending wire 161*d*) for bending the bending portion 112 in the UD direction to the drive device 200.

The horizontal bending wire attachment/detachment portion 152 is a mechanism for detachably connecting the wires (the left bending wire 161*l* and the right bending wire 161*r*) for bending the bending portion 112 in the LR direction to the drive device 200.

The horizontal bending wire attachment/detachment portion 152 has the same structure as the vertical bending wire attachment/detachment portion 151, so illustration and description thereof are omitted.

Figure 8:
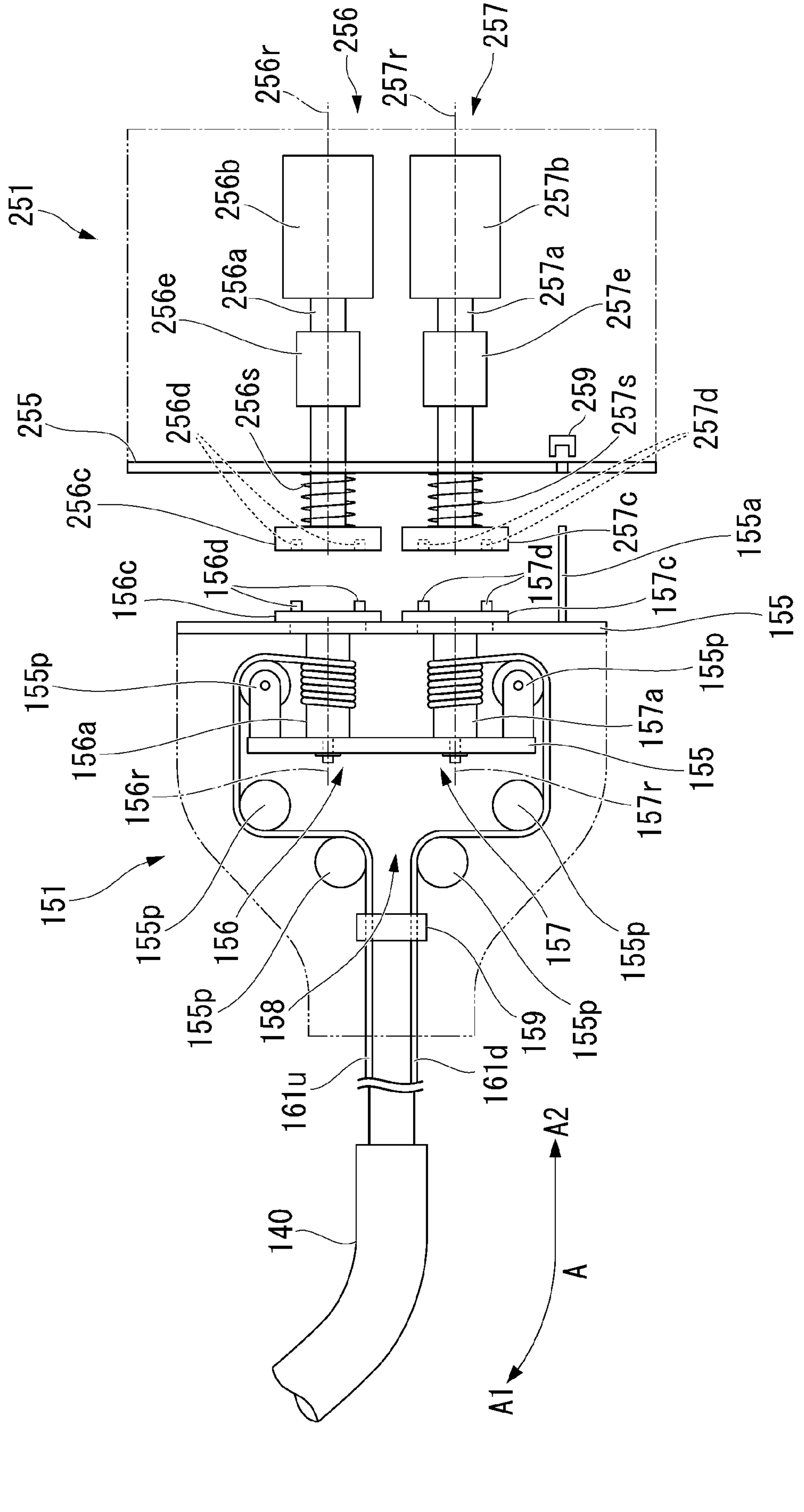
FIG. 8 is a view showing a first vertical bending wire attachment/detachment portion before being attached to the drive device.
Figure 9:
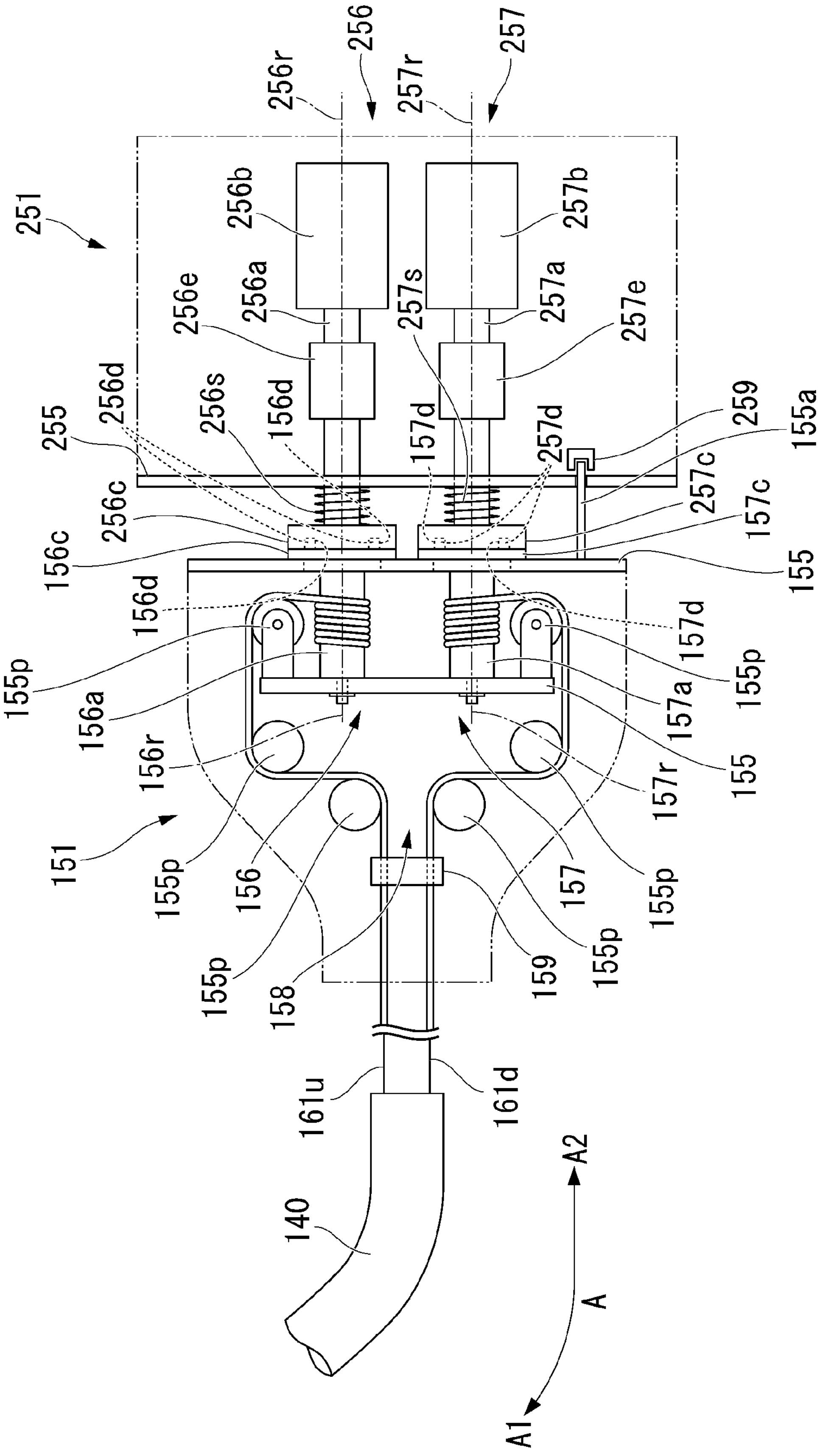
FIG. 9 is a diagram showing the first vertical bending wire attachment/detachment portion attached to the drive device.

FIG. 8 is a diagram showing the vertical bending wire attachment/detachment portion 151 before being attached to the drive device 200. FIG. 9 is a diagram showing the vertical bending wire attachment/detachment portion 151 attached to the drive device 200. The vertical bending wire attachment/detachment portion 151 has a support member 155, a first rotating drum 156, a second rotating drum 157, and a tension sensor 159.

The support member 155 supports the first rotating drum 156, the second rotating drum 157, and the connecting member 158. The support member 155 has an attachment/detachment detection dog 155*a* exposed on the proximal end side of the vertical bending wire attachment/detachment portion 151, and a plurality of bend pulleys 155*p*.

The bend pulley 155*p* changes the conveying direction of the upper bending wire 161*u* inserted through the extracorporeal flexible portion 140, and guides the upper bending wire 161*u* to the first rotating drum 156. The bend pulley 155*p* changes the conveying direction of the lower bending wire 161*d* inserted through the extracorporeal flexible portion 140 and guides the lower bending wire 161*d* to the second rotating drum 157.

The first rotating drum 156 is supported by the support member 155 so as to be rotatable around a first drum rotating shaft 156*r* extending along the longitudinal direction A. The first rotating drum 156 has a first winding pulley 156*a* and a first coupling portion 156*c*.

The first winding pulley 156*a* pulls or feeds the upper bending wire (first bending wire) 161*u* by rotating around the first drum rotating shaft 156*r*. As the first winding pulley 156*a* rotates clockwise when viewed from the distal end side to the proximal end side, the upper bending wire 161*u* is wound around the first winding pulley 156*a* and pulled. Conversely, by rotating the first winding pulley 156*a* counterclockwise, the upper bending wire 161*u* is sent out from the first winding pulley 156*a*. With this configuration, even if the upper bending wire 161*u* moves forward and backward, the towed portion is stored compactly and does not take up much space.

The first coupling portion 156*c* is a disc member that rotates about the first drum rotating shaft 156*r*. The first coupling portion 156*c* is fixed to the proximal end of the first winding pulley 156*a*, and rotates integrally with the first winding pulley 156*a*. The first coupling portion 156*c* is exposed on the proximal end side of the vertical bending wire attachment/detachment portion 151. Two first fitting protrusions 156*d* are formed on the proximal end side surface of the first coupling portion 156*c*. The two first fitting protrusions 156*d* are formed on both sides of the first drum rotating shaft 156*r*.

The second rotating drum 157 is supported by the supporting member 155 so as to be rotatable around a second drum rotating shaft 157*r* extending along the longitudinal direction A. The second rotating drum 157 has a second winding pulley 157*a* and a second coupling portion 157*c*.

The second winding pulley 157*a* pulls or feeds the lower bending wire (second bending wire) 161*d* by rotating around the second drum rotating shaft 157*r*. As the second winding pulley 157*a* rotates counterclockwise when viewed from the distal end side to the proximal end side, the lower bending wire 161*d* is wound around the second winding pulley 157*a* and pulled. Conversely, the clockwise rotation of the second winding pulley 157*a* feeds the lower bending wire 161*d* from the second winding pulley 157*a*.

The second coupling portion 157*c* is a disc member that rotates about the second drum rotating shaft 157*r*. The second coupling portion 157*c* is fixed to the proximal end of the second winding pulley 157*a*, and rotates integrally with the second winding pulley 157*a*. The second coupling portion 157*c* is exposed on the proximal end side of the vertical bending wire attachment/detachment portion 151. Two second fitting protrusions 157*d* are formed on the proximal end side surface of the second coupling portion 157*c*. The two second fitting protrusions 157*d* are formed on both sides of the second drum rotating shaft 157*r*.

The tension sensor 159 detects the tension of the upper bending wire 161*u* and the lower bending wire 161*d*. A detection result of the tension sensor 159 is acquired by a drive controller 260.

[Drive Device 200]

Figure 10:
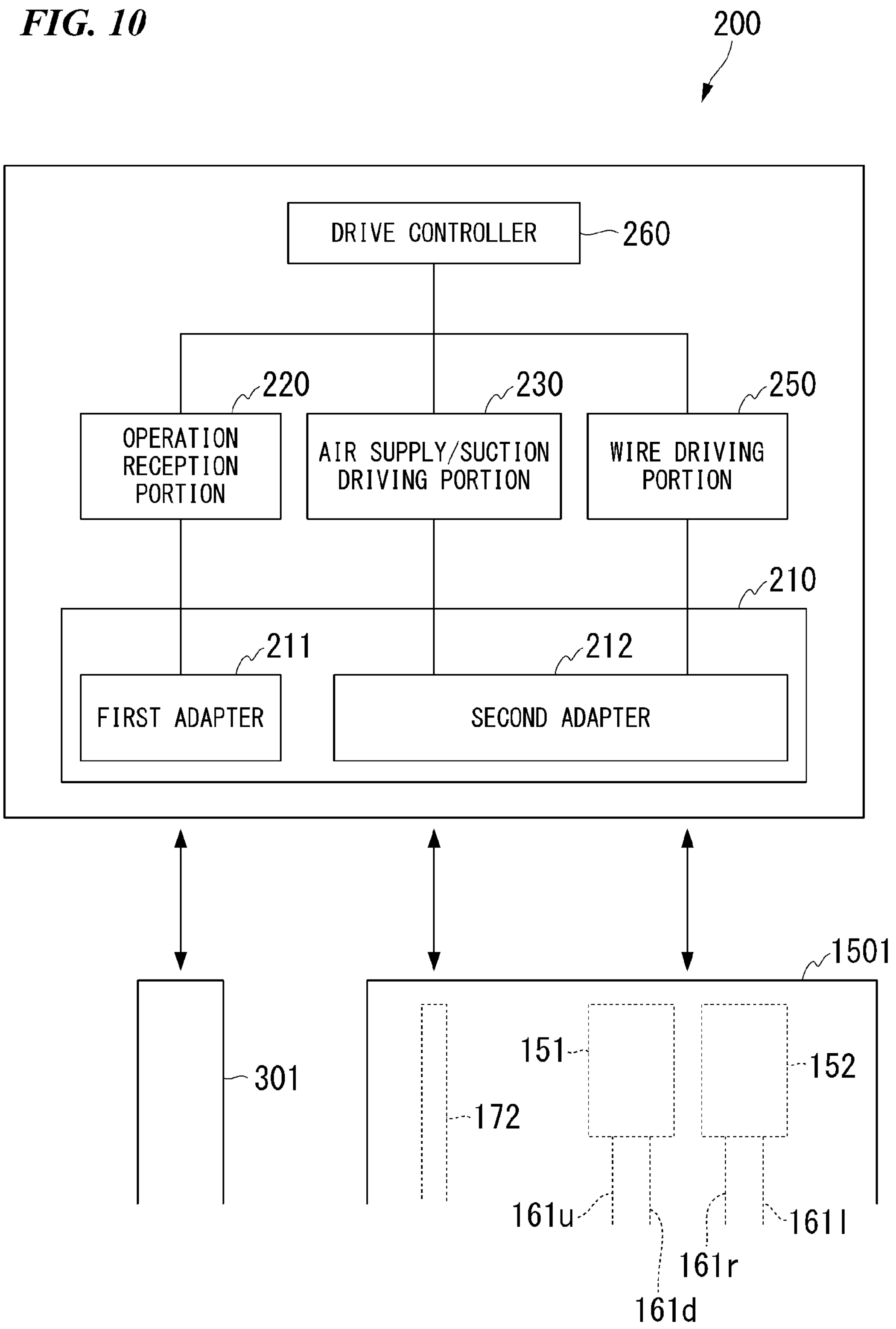
FIG. 10 is a functional block diagram of a drive device of the electric endoscope system.

FIG. 10 is a functional block diagram of the drive device 200.

The drive device 200 includes an adapter 210, an operation reception portion 220, an air supply/suction driving portion 230, a wire driving portion 250 and the drive controller 260.

The adapter 210 has a first adapter 211 and a second adapter 212, as shown in FIG. 7. The first adapter 211 is an adapter to which the operation cable 301 is detachably connected. The second adapter 212 is an adapter to which the first attachment/detachment portion 1501 of the endoscope 100 is detachably connected.

The operation reception portion 220 receives operation input from the operation device 300 via the operation cable 301. When the operation device 300 and the drive device 200 communicate with each other not by wired communication but by wireless communication, the operation reception portion 220 has a known wireless reception module.

The air supply/suction driving portion 230 is connected to the air supply/suction tube 172 inserted into the internal path 101 of the endoscope 100. The air supply/suction driving portion 230 includes a pump and the like, and supplies air to the air supply/suction tube 172. Also, the air supply/suction driving portion 230 sucks air from the air supply/suction tube 172.

The wire driving portion 250 drives the bending wire 160 by coupling with the vertical bending wire attachment/detachment portion 151 and the horizontal bending wire attachment/detachment portion 152.

The wire driving portion 250 has a vertical bending wire driving portion 251 and a horizontal bending wire driving portion 252, as shown in FIG. 7.

The vertical bending wire driving portion 251 is a mechanism that is coupled with the vertical bending wire attachment/detachment portion 151 to drive the wires (the upper bending wire 161*u* and the lower bending wire 161*d*) that bend the bending portion 112 in the UD direction.

The vertical bending wire driving portion 252 is a mechanism that is coupled with the horizontal bending wire attachment/detachment portion 152 to drive the wires (the left bending wire 161*l* and the right bending wire 161*r*) that bend the bending portion 112 in the LR direction.

The vertical bending wire driving portion 252 has the same structure as the vertical bending wire driving portion 251, so illustration and description thereof will be omitted.

The vertical bending wire driving portion 251 includes a support member 255, an upper bending wire driving portion 256, a lower bending wire driving portion 257, and an attachment/detachment sensor 259, as shown in FIG. 8.

The upper bending wire driving portion 256 is coupled with the first rotary drum 156 of the vertical bending wire attachment/detachment portion 151 to drive the upper bending wire 161*u*. The upper bending wire driving portion 256 has a first shaft 256*a*, a first motor portion 256*b*, a first coupled portion 256*c*, a first torque sensor 256*e*, and a first elastic member 256*s*.

The first shaft 256*a* is supported by the support member 255 so as to be rotatable about the first shaft rotation axis 256*r* and to be advanced and retracted in the longitudinal direction A. When the first attachment/detachment portion 1501 of the endoscope 100 is attached to the drive device 200, the first shaft rotation axis 256*r* coincides with the first drum rotation axis 156*r*.

The first motor portion 256*b* has a first motor such as a DC motor, a first motor driver that drives the first motor, and a first motor encoder. The first motor rotates the first shaft 256*a* around the first shaft rotation axis 256*r*. The first motor driver is controlled by the drive controller 260.

The first coupled portion 256*c* is a disk member that rotates around the first shaft rotation axis 256*r*. The first coupled portion 256*c* is fixed to the distal end of the first shaft 256*a* and rotates integrally with the first shaft 256*a*. As shown in FIG. 8, the first coupled portion 256 *c* is exposed at the distal end side of the vertical bending wire driving portion 251. Two first fitting recesses 256*d* are formed on the front end side surface of the first coupled portion 256*c*. The two first fitting recesses 256*d* are formed on both sides of the first shaft rotation axis 256*r*.

As shown in FIG. 9, the first fitting protrusions 156*d* and the first fitting recesses 256*d* are fitted to couple the first coupling portion 156*c* and the first coupled portion 256*c*. As a result, the rotation of the first shaft 256*a* by the first motor portion 256*b* is transmitted to the first rotary drum 156. The upper bending wire 161*u* is pulled by rotating the first shaft 256*a* clockwise when viewed from the distal end side to the proximal end side. Conversely, the upper bending wire 161*u* is delivered by rotating the first shaft 256*a* counterclockwise.

The first torque sensor 256*e* detects the rotational torque of the first shaft 256*a* around the first shaft rotation axis 256*r*. A detection result of the first torque sensor 256*e* is acquired by the drive controller 260.

The first elastic member 256*s* is, for example, a compression spring, and has a distal end in contact with the first coupled portion 256*c* and a proximal end in contact with the supporting member 255. The first elastic member 256*s* biases the first coupled portion 256*c* toward the distal end side (A1). As shown in FIG. 9, when the first coupling portion 156*c* is attached, the first coupled portion 256*c* moves toward the proximal end side (A2) together with the first shaft 256*a*.

The lower bending wire driving portion 257 is coupled with the second rotary drum 157 of the vertical bending wire attachment/detachment portion 151 to drive the lower bending wire 161*d*. The lower bending wire driving portion 257 has a second shaft 257*a*, a second motor portion 257*b*, a second coupled portion 257*c*, a second torque sensor 257*e*, and a second elastic member 257*s*.

The second shaft 257*a* is supported by the support member 255 so as to be rotatable about a second shaft rotation axis 257*r* and to be advanced and retracted in the longitudinal direction A. When the first attachment/detachment portion 1501 of the endoscope 100 is attached to the drive device 200, the second shaft rotation axis 257*r* coincides with the second drum rotation axis 157*r*.

The second motor portion 257*b* has a second motor such as a DC motor, a second motor driver that drives the second motor, and a second motor encoder. The second motor rotates the second shaft 257*a* around the second shaft rotation axis 257*r*. The second motor driver is controlled by drive controller 260.

The second coupled portion 257*c* is a disc member that rotates around the second shaft rotation axis 257*r*. The second coupled portion 257*c* is fixed to the distal end of the second shaft 257*a* and rotates integrally with the second shaft 257*a*. As shown in FIG. 8, the second coupled portion 257*c* is exposed at the distal end side of the vertical bending wire driving portion 251. Two second fitting recesses 257*d* are formed on the front end side surface of the second coupled portion 257*c*. The two second fitting recesses 257*d* are formed on both sides of the second shaft rotating shaft 257*r*.

As shown in FIG. 9, the second fitting protrusions 157*d* and the second fitting recesses 257*d* are fitted to couple the second coupling portion 157*c* and the second coupled portion 257*c*. As a result, the rotation of the second shaft 257*a* by the second motor portion 257*b* is transmitted to the second rotating drum 157. The lower bending wire 161*d* is pulled by rotating the second shaft 257*a* counterclockwise when viewed from the distal end side to the proximal end side. Conversely, the lower bending wire 161*d* is delivered by rotating the second shaft 257*a* clockwise.

The second torque sensor 257*e* detects the rotational torque of the second shaft 257*a* about the second shaft rotation axis 257*r*. A detection result of the second torque sensor 257*e* is acquired by the drive controller 260.

The second elastic member 257*s* is, for example, a compression spring, and has a distal end portion contacting the second coupled portion 257*c* and a proximal end portion contacting the support member 255. The second elastic member 257*s* biases the second coupled portion 257*c* toward the distal end side (A1). As shown in FIG. 9, when the second coupling portion 157*c* is attached, the second coupled portion 257*c* moves toward the proximal end side (A2) together with the second shaft 257*a*.

As shown in FIG. 9, the attachment/detachment sensor 259 detects attachment/detachment of the vertical bending wire attachment/detachment portion 151 to/from the vertical bending wire driving portion 251 by detecting engagement and disengagement with the attachment/detachment detection dog 155*a*. The detection result of the attachment/detachment sensor 259 is acquired by the drive controller 260.

With the above mechanism, when the vertical bending wire attachment/detachment portion 151 is attached to the vertical bending wire driving portion 251, the upper bending wire driving portion 256 can independently drive the upper bending wire 161*u*, and the lower bending wire driving portion 257 can independently drive the lower bending wire 161*d*. Therefore, even if the distance from the bending portion 112 of the endoscope 100 to the drive device 200 is longer than that of the conventional flexible endoscope, the bending operation of the bending portion 112 can be controlled with high accuracy.

The drive controller 260 controls the drive device 200 as a whole. The drive controller 260 acquires the operation input received by the operation reception portion 220. The drive controller 260 controls the air supply/suction driving portion 230 and the wire driving portion 250 based on the acquired operation input.

The drive controller 260 is a program-executable computer including a processor, a memory, a storage portion capable of storing programs and data, and an input/output control portion. The functions of the drive controller 260 are implemented by the processor executing a program. At least some functions of the drive controller 260 may be realized by dedicated logic circuits.

The drive controller 260 desirably has high computational performance in order to control the plurality of motors that drive the plurality of bending wires 160 with high accuracy.

It should be noted that the drive controller 260 may further have a configuration other than the processor, memory, storage portion, and input/output control portion. For example, the drive controller 260 may further include an image calculation portion that performs some or all of the image processing and image recognition processing. By further including an image calculation portion, the drive controller 260 can perform specific image processing and image recognition processing at high speed. The image calculation portion may be mounted in a separate hardware device connected via a communication line.

[Operation Device 300]

The operation device 300 is a device to which an operation for driving the endoscope 100 is input. The input operation input is transmitted to the drive device 200 via the operation cable 301.

[Video Control Device 500]

Figure 11:
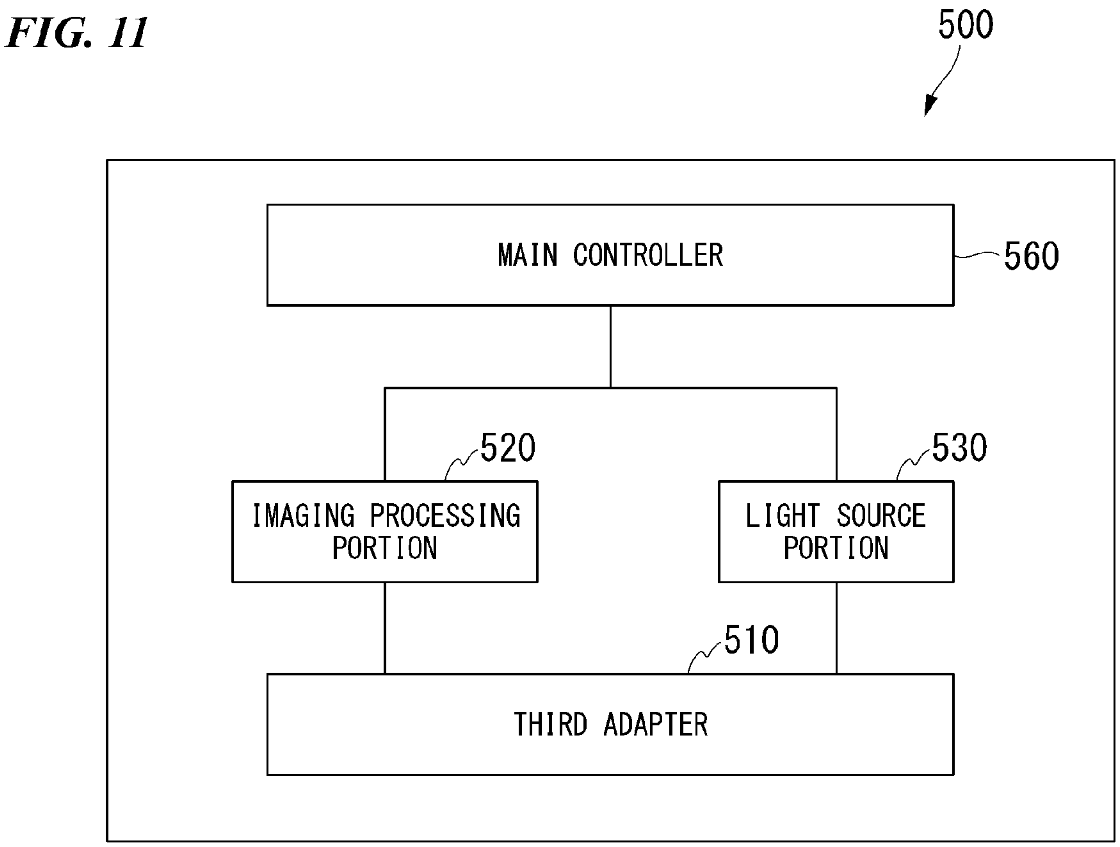
FIG. 11 is a functional block diagram of a control device of the electric endoscope system.

FIG. 11 is a functional block diagram of the video control device 500.

The image control device 500 controls the electric endoscope system 1000. The video control device 500 includes a third adapter 510, an imaging processing portion 520, a light source portion 530 and a main controller 560.

The third adapter 510 is an adapter to which the second attachment/detachment portion 1502 of the endoscope 100 is detachably connected.

The imaging processing portion 520 converts an imaging signal acquired from the imaging portion 111*c* of the distal end portion 1 via the imaging cable 173 into a captured image.

The light source portion 530 generates illumination light that irradiates the object to be imaged. The illumination light generated by the light source portion 530 is guided to the illumination portion 111*b* of the distal end portion 111 via the light guide 174.

Figure 12:
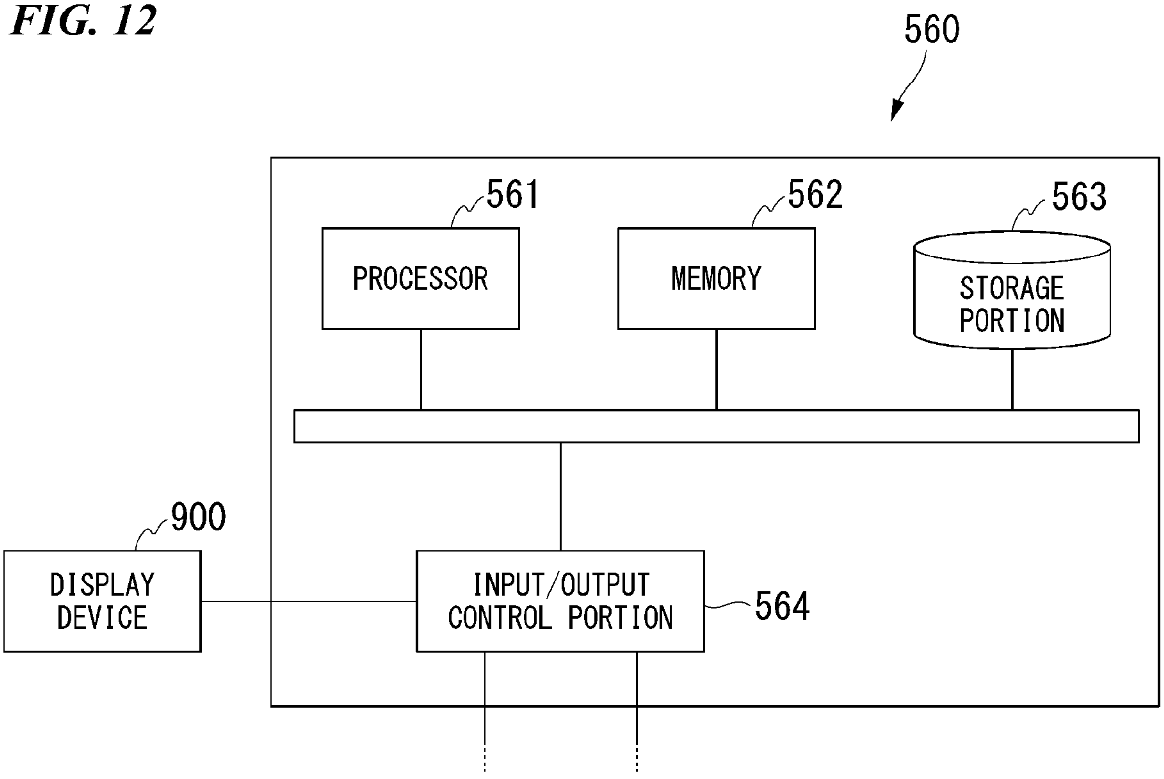
FIG. 12 is a functional block diagram of a main controller of the control device.

FIG. 12 is a functional block diagram of the main controller 560.

The main controller 560 is a program-executable computer having a processor 561, a memory 562, and the like. The functions of the main controller 560 are implemented by the processor 561 executing programs. At least some of the functions of the main controller 560 may be realized by a dedicated logic circuit.

The main controller 560 has the processor 561, the memory 562, a storage portion 563, and an input/output control portion 564.

The storage portion 563 is a non-volatile recording medium that stores the above-described programs and necessary data. The storage portion 563 is composed of, for example, a ROM, a hard disk, or the like. A program recorded in the storage portion 563 is read into the memory 562 and executed by the processor 561.

The input/output control portion 564 is connected to the imaging processing portion 520, the light source portion 530, the drive device 200, the display device 900, the input device (not shown), and the network device (not shown). Under the control of the processor 561, the input/output control portion 564 transmits and receives data and control signals to and from connected devices.

The main controller 560 can perform image processing on the captured image acquired by the imaging processing portion 520. The main controller 560 can generate GUI images and CG images for the purpose of providing information to the surgeon S. The main controller 560 can display captured images, GUI images, and CG images on the display device 900.

The main controller 560 is not limited to an integrated hardware device. For example, the main controller 560 may be configured by separating a part of it as a separate hardware device and then connecting the separated hardware device with a communication line. For example, the main controller 560 may be a cloud system that connects separated storage portions 563 via communication lines.

The main controller 560 may further have a configuration other than the processor 561, the memory 562, the storage portion 563, and the input/output control portion 564 shown in FIG. 12. For example, the main controller 560 may further have an image calculation portion that performs some or all of the image processing and image recognition processing that the processor 561 has performed. By further having an image calculation portion, the main controller 560 can execute specific image processing and image recognition processing at high speed. The image calculation portion may be mounted in a separate hardware device connected via a communication line.

[Observation Device 800]

The observation device 800 is a device that observes the insertion shape of the endoscope 100 using a magnetic field. The observation device 800 receives magnetism generated by a magnetic coil built into the insertion portion 110 of the endoscope 100 with an antenna. Observation results of the observation device 800 are also acquired by the main controller 560.

[Operation of the Electric Endoscope System 1000]

Next, the operation of the electric endoscope system 1000 of this embodiment will be described. Specifically, a procedure for observing and treating an affected area formed on the wall of the large intestine using the electric endoscope system 1000 will be described.

Figure 13:
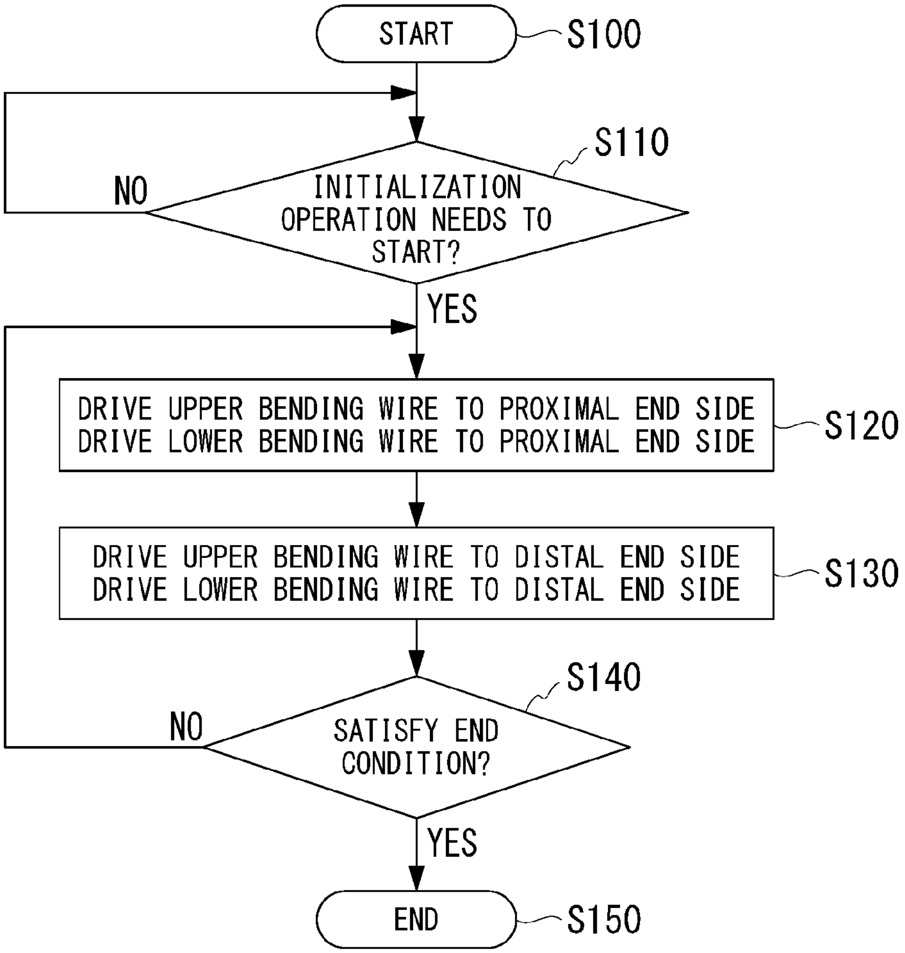
FIG. 13 is a flowchart showing control of the main controller in the control device of the electric endoscope system.

Hereinafter, description will be given with reference to the flowchart showing control of the main controller 560 of the control device 600 shown in FIG. 13. When the control device 600 is activated, the main controller 560 starts control after performing initialization (step S100). Next, the main controller 560 (mainly the processor 561) executes step S110.

<Step S110; Determining Start of Initialization Operation>

In step S110, the main controller 560 periodically checks the state of the power transmission system of the endoscope 100 and determines the start of the initialization operation of the power transmission system. The main controller 560 can improve the power transmission efficiency of the power transmission system by performing the initialization operation of the power transmission system and optimizing the state of the power transmission system. Here, the transmission efficiency of the power transmission system is the ratio of the output tension to the input tension to the bending wire 160, or the like.

The "power transmission system" is a member that connects the wire driving portion 250 and the bending portion 112 and that transmits power for bending the bending portion 112. In this embodiment, the "power transmission system" is the wire driving portion 250, the vertical bending wire attachment/detachment portion 151 or the horizontal bending wire attachment/detachment portion 152, and the bending wire 160.

Figure 14:
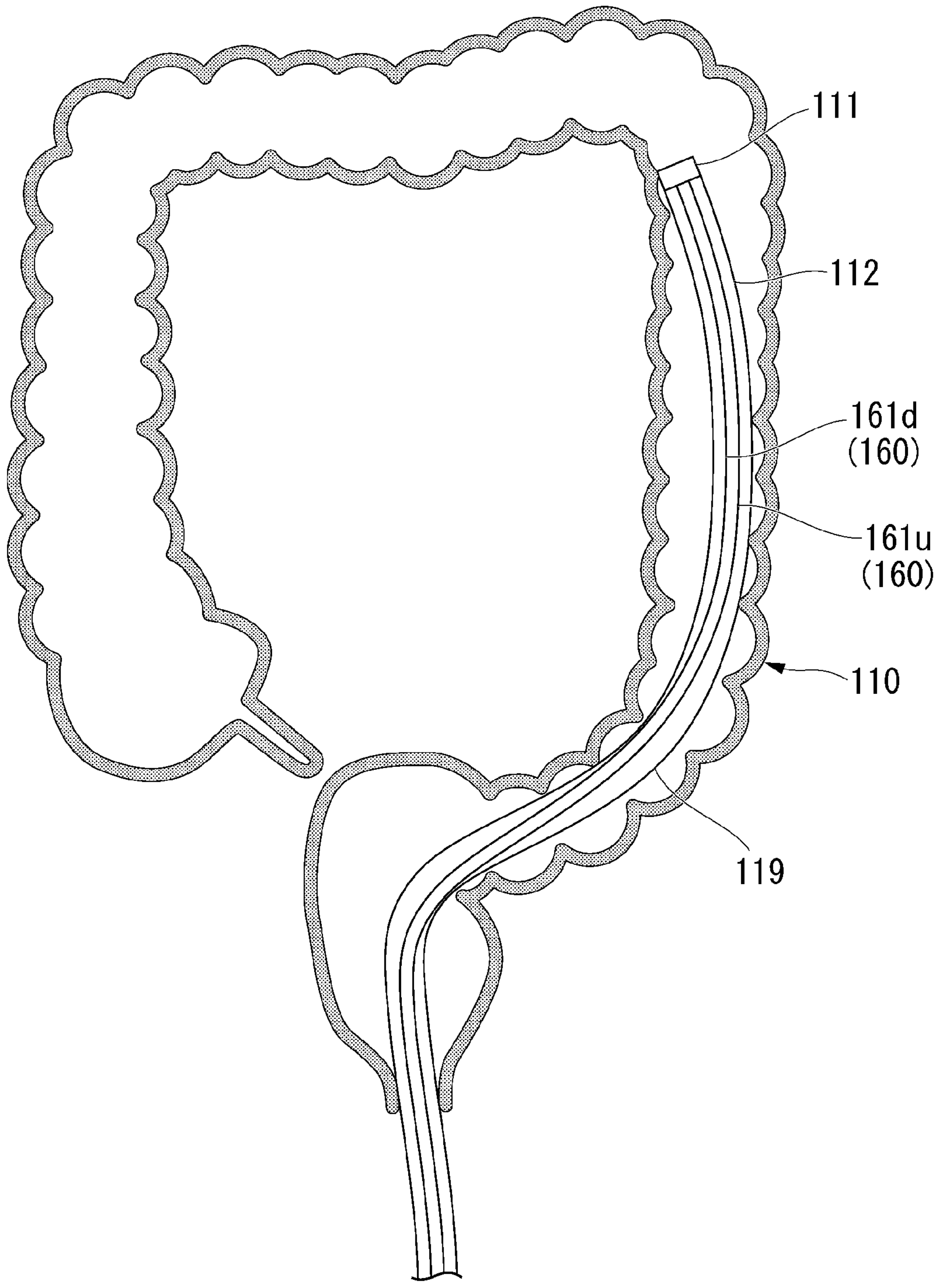
FIG. 14 is a diagram showing the insertion portion inserted into the large intestine.

FIG. 14 is a diagram showing the insertion portion 110 inserted into the large intestine.

The surgeon S inserts the insertion portion 110 of the endoscope 100 into the large intestine through the anus of the patient P. The surgeon S moves the insertion portion 110 to bring the distal end portion 111 closer to the affected area while observing the captured image displayed on the display device 900 and operating the internal flexible portion 119 with the right hand R. Further, the surgeon S operates the operation device 300 with the left hand L to bend the bending portion 112 as necessary.

Figure 15:
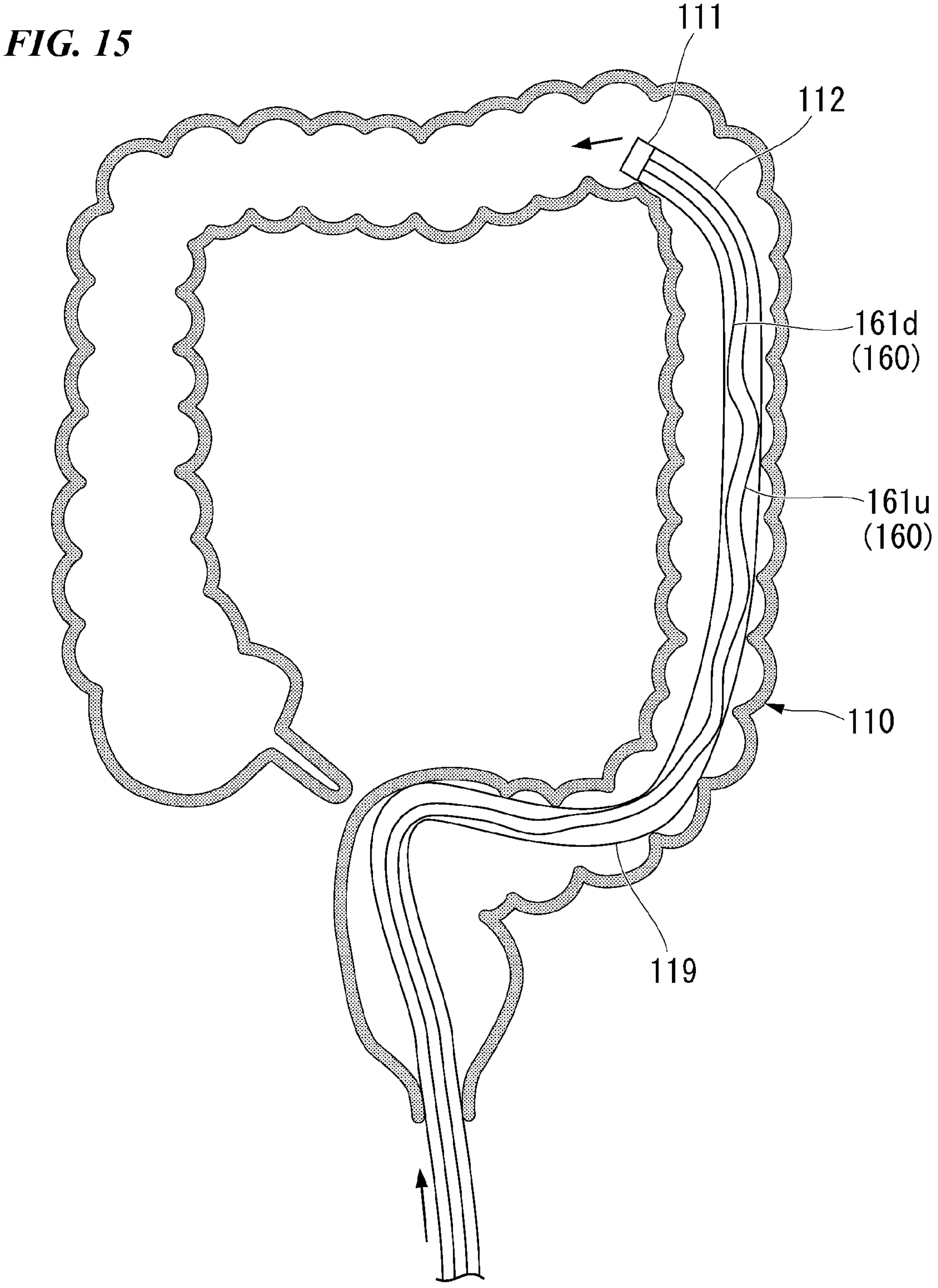
FIG. 15 is a diagram showing the insertion portion with a greatly changed shape.

FIG. 15 is a diagram showing the insertion portion 110 whose shape has changed significantly.

The main controller 560 acquires the shape of the insertion portion 110 from the observation device 800. When the acquired shape of the insertion portion 110 (for example, the shape of the insertion portion 110 shown in FIG. 15) has changed compared with the shape of the insertion portion 110 acquired before a predetermined period (for example, the shape of the insertion portion 110 shown in FIG. 14), the main controller 560 determines that it is necessary to start the initialization operation of the power transmission system.

When the shape of the insertion portion 110 changes, the state of the power transmission system of the endoscope 100 may not be optimized. For example, as shown in FIG. 15, due to the influence of the shape change of the insertion portion 110, the upper bending wire **161*u* and the lower bending wire 161*d* passing through the internal path 101 of the insertion portion 110 may sag. In this case, the path of the upper bending wire 161*u* and the lower bending wire 161*d* is not the shortest path with respect to the shape of the insertion portion 110**.

For example, when the obtained total bending angle of the shape of the insertion portion 110 exceeds a predetermined threshold value, the main controller 560 determines that the shape of the insertion portion 110 has changed, and determines that it is necessary to start the initialization operation of the power transmission system.

The method by which the main controller 560 acquires the shape of the insertion portion 110 is not limited to the method of acquiring from the observation device 800. The main controller 560 may acquire the shape of the insertion portion 110 from, for example, an optical fiber inserted through the internal path 101 of the insertion portion 110. Further, when the amount of operation input to the operation device 300 by the surgeon S exceeds a predetermined threshold value, the initialization operation may be started. Alternatively, the initialization operation may be started when the wire tension obtained from the tension sensor 159 or the pulling amount obtained from the motor encoder exceeds a predetermined amount.

Before driving the bending portion 112 of the endoscope 100, it is desirable that the power transmission efficiency of the power transmission system be improved by performing the initialization operation of the power transmission system to optimize the state of the power transmission system. Therefore, when the treatment tool sensor **111*d* provided at the distal end portion 11 of the insertion portion 110 detects the treatment tool 400, the main controller 560 may determine that the bending portion 112 of the endoscope 100** is likely to be driven next, and that it is necessary to start the initialization operation of the power transmission system.

The main controller 560 may start the initialization operation of the power transmission system based on a predetermined operation of the operation device 300 by the surgeon S. Also, the main controller 560 may start the initialization operation of the power transmission system at predetermined intervals.

When the main controller 560 determines that the power transmission system needs to be initialized, it then executes step S120.

<Step S120: First Step of Initialization Operation>

The main controller 560 drives the first motor portion **256*b* to rotate the first shaft 256*a* by controlling the drive controller 260 in step S120. By rotating the first shaft 256*a* clockwise when viewed from the distal end side to the proximal end side, the upper bending wire 161*u* is pulled. As a result, the upper bending wire 161*u* moves to the proximal end side (A2**).

In step S120, the main controller 560 controls the drive controller 260 to drive the second motor portion **257*b* to rotate the second shaft 257*a*. By rotating the second shaft 257*a* counterclockwise when viewed from the distal end side to the proximal end side, the lower bending wire 161*d* is pulled. As a result, the lower bending wire 161*d* moves to the proximal end side (A2**).

Figure 16:
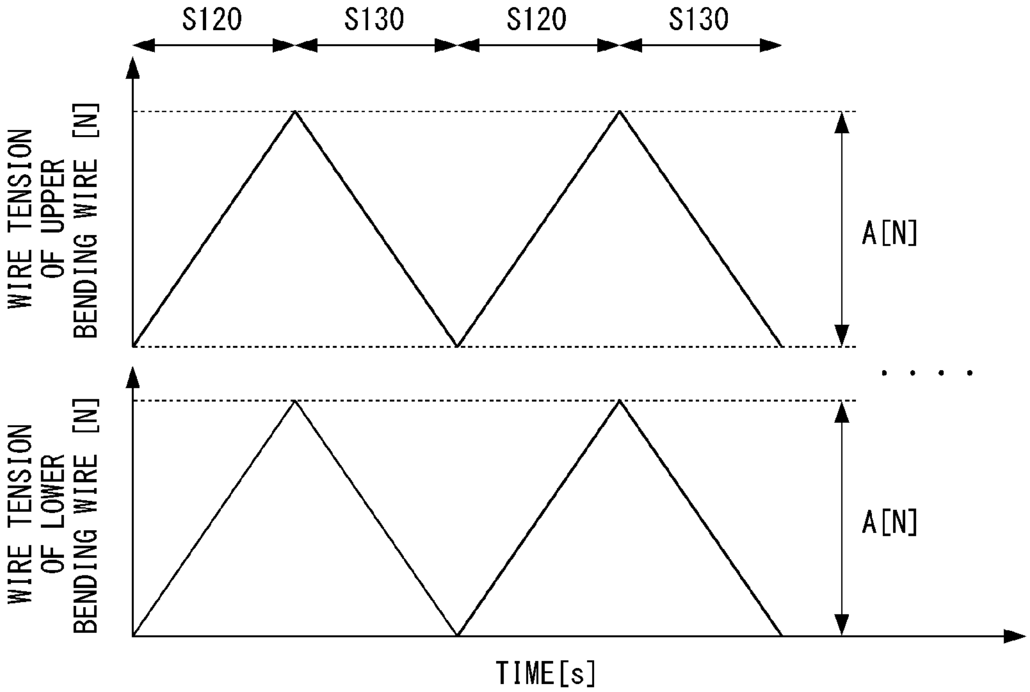
FIG. 16 is a graph showing the tension of the bending wire controlled by the main controller.

FIG. 16 is a graph showing the tension of the upper bending wire **161*u* and the lower bending wire 161*d*. The main controller 560 simultaneously drives the upper bending wire 161*u* and the lower bending wire 161*d*. The main controller 560 acquires the tension of the upper bending wire 161*u* and the tension of the lower bending wire 161*d* from the tension sensor 159. The main controller 560 controls the first motor portion 256*b* and the second motor portion 257*b* to substantially match the amount of change in the tension of the upper bending w % ire 161*u* and the amount of change in the tension of the lower bending wire 161*d*. It should be noted that the origin of the graph shown in FIG. 16** is not necessarily zero tension, but the origin is the tension of each wire at the time of execution of the initialization operation.

The main controller 560 increases the tension of the upper bending wire **161*u* and the tension of the lower bending wire 161*d* at a rate of B [N/s], to become A[N]. The main controller 560 determines the tension A[N] so that the bending amount of the bending portion 112 is within a predetermined range. The amount of bending of the bending portion 112 is, for example, the amount of change in the bending shape of the bending portion 112 and the amount of change in the bending angle of the bending portion 112 compared to when the initial operation is started. Specifically, it is thought that a change in the field of view of about 20% can be corrected and treated by a doctor's operation, and the main controller 560 determines the tension A[N] so that the change in the field of view of the imaging portion 111*c* is 20% or less. More preferably, the tension A[N] is determined so that the change in visual field is 15% or less. More preferably, the tension A[N] is determined so that the change in visual field is 5% or less. The imaging portion 111 is provided on the distal end side (A1) of the bending portion 112, and the field of view captured by the imaging portion 111 changes as the bending portion 112 bends. Therefore, the main controller 560 can recognize the bending amount of the bending portion 112 based on the change in the field of view captured by the imaging portion 111. The main controller 560 then executes step S130**.

<Step S130: Second Step of Initialization Operation>

The main controller 560 drives the first motor portion 256*b* to rotate the first shaft 256*a* by controlling the drive controller 260 in step S130. By rotating the first shaft 256*a* counterclockwise when viewed from the distal end to the proximal end, the upper bending wire 161*u* is loosened. As a result, the upper bending wire 161*u* moves to the distal end side (A1).

The main controller 560 drives the second motor portion 257*b* to rotate the second shaft 257*a* by controlling the drive controller 260 in step S130. By rotating the second shaft 257*a* clockwise when viewed from the distal end to the proximal end, the lower bending wire 161*d* is loosened. As a result, the lower bending wire 161*d* moves to the distal end side (A1).

As shown in FIG. 16, the main controller 560 simultaneously drives the upper bending wire 161*u* and the lower bending wire 161*d*. The main controller 560 acquires the tension of the upper bending wire 161*u* and the tension of the lower bending wire 161*d* from the tension sensor 159. The main controller 560 controls the first motor portion 256*b* and the second motor portion 257*b* to substantially match the amount of change in the tension of the upper bending wire 161*u* and the amount of change in the tension of the lower bending wire 161*d*.

The main controller 560 decreases the tension of the upper bending wire 161*u* and the tension of the lower bending wire 161*d* at a rate of B [N/s], to become A[N]. The rate and amount of change in tension in step S130 are the same as the rate and amount of change in tension in step S120. The main controller 560 then executes step S140.

<Step S140: Determination of End of Initialization Operation>

In step S140, the main controller 560 determines whether the initialization operation of the power transmission system is finished. When the main controller 560 determines that the state of the power transmission system is sufficiently optimized, it ends the initialization operation of the power transmission system.

Figure 17:
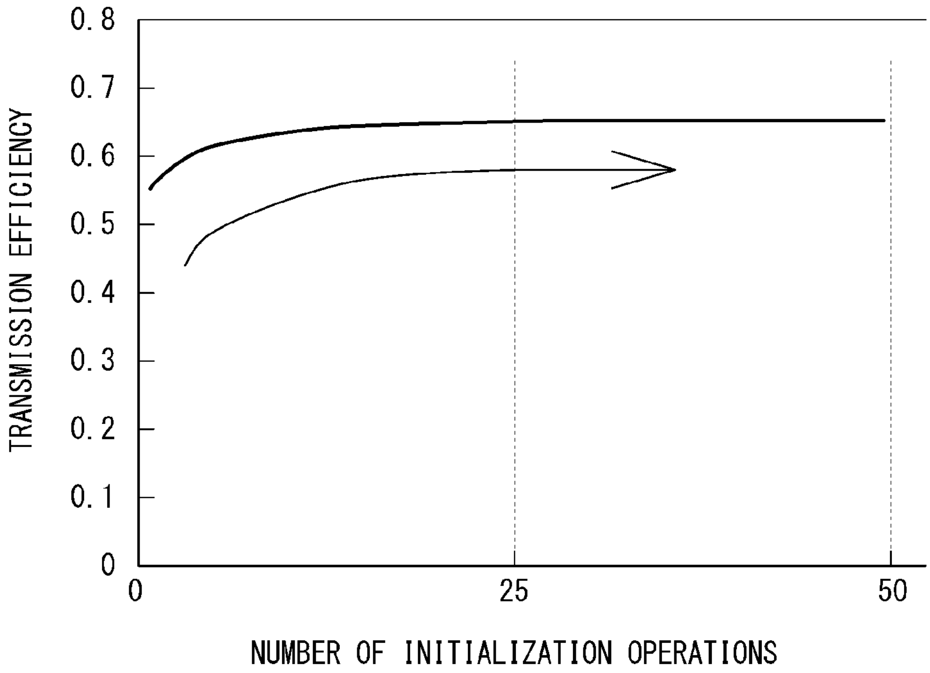
FIG. 17 shows measurement results of the number of initialization operations and the power transmission efficiency of the power transmission system.

FIG. 17 shows the measurement results of the number of initialization operations and the power transmission efficiency of the power transmission system.

According to the measurement results shown in FIG. 17, the power transmission efficiency of the power transmission system is sufficiently improved after performing the initialization operation several tens of times. The main controller 560 sets the number of initialization operations required to sufficiently improve the power transmission efficiency of the power transmission system as the "minimum number of times N" based on the results of measurements performed in advance. When the number of initialization operations has reached the minimum number N, the main controller 560 determines that the initialization operation of the power transmission system may be terminated. The number of initialization operations is the number of times when the combination of steps S120 and S130 is counted as one.

In step S140, the main controller 560 compares the number of initialization operations performed after step S110 with the minimum number of times N. If the number of initialization operations is less than the minimum number N, the main controller 560 performs steps S120 and S130 again. If the number of initialization operations is equal to the minimum number of times N, the main controller 560 performs step S150 to end the initialization operation.

Figure 18:
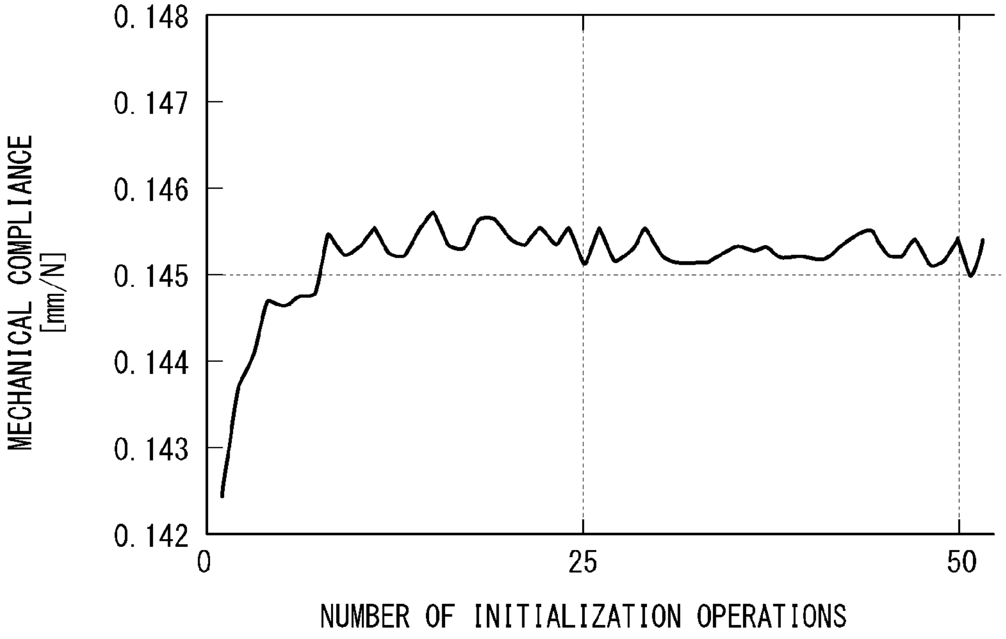
FIG. 18 shows measurement results of the number of initialization operations and mechanical compliance.

FIG. 18 shows the measurement results of the number of initialization operations and mechanical compliance.

The mechanical compliance is the reciprocal of the spring constant calculated from the wire tension obtained from the tension sensor 159 and the pulling amount obtained from the first motor encoder of the first motor portion 256*b*. The measurement results of the mechanical compliance shown in FIG. 18 show a tendency similar to the measurement results of the power transmission efficiency of the power transmission system shown in FIG. 17. Therefore, the main controller 560 may use the calculated mechanical compliance to determine the end of the initialization operation. The main controller 560 may determine that the initialization operation of the power transmission system may be terminated when the calculated mechanical compliance becomes greater than a predetermined value. By using the mechanical compliance calculated from the wire tension and pulling amount acquired in step S140, the main controller 560 can determine the end of the initialization operation in consideration of the actual state of the power transmission system.

Figure 19:
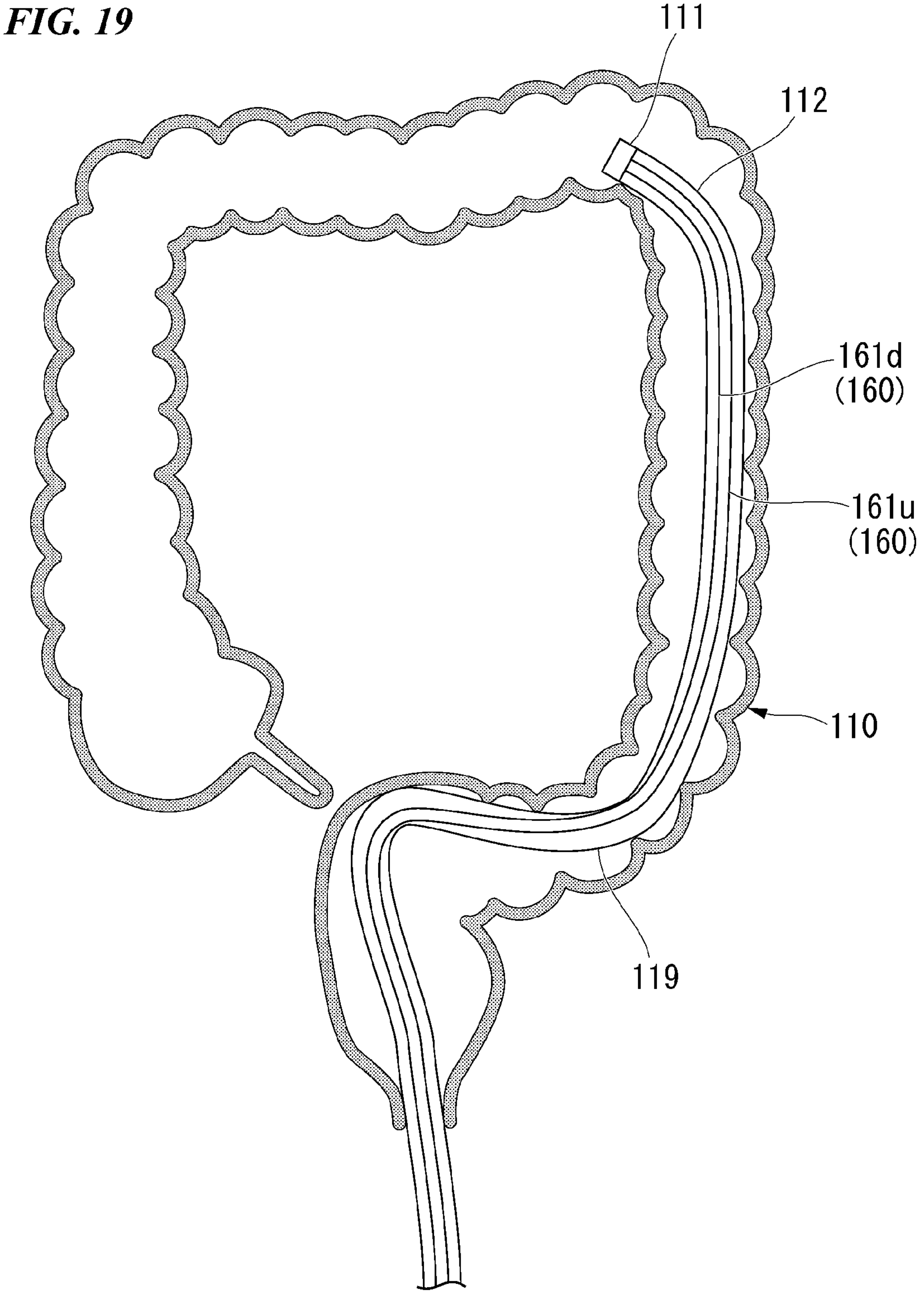
FIG. 19 is a diagram showing the insertion portion after the initialization operation is completed.

FIG. 19 is a diagram showing the inserting portion 110 after the initialization operation is completed.

When the initialization operation is completed, the paths of the upper bending wire 161*u* and the lower bending wire 161*d* are the shortest paths with respect to the shape of the insertion portion 110, as shown in FIG. 19. As a result, the power transmission efficiency of the power transmission system is improved.

When the initialization operation is finished, the coating on the surface of the bending wire 160 is adapted, and the coefficient of friction between the inner peripheral surface of the wire sheath 161*s* and the bending wire 160 and the coefficient of friction between the wire sheaths 161*s* decrease. As a result, the power transmission efficiency of the power transmission system is improved.

Since step S120 and step S130 are alternately performed, the amount of bending of the bending portion 112 after the initialization operation substantially matches the amount of bending of the bending portion 112 before the start of the initialization operation.

The main controller 560 also performs a similar initialization operation for the pair of bending wires 160 (the left bending wire 161*l* and the right bending wire 161*r*) that bend the bending portion 112 in the vertical direction (LR direction). The initialization operations for the left bending wire 161*l* and the right bending wire 161*r* may be performed simultaneously with the initialization operations for the upper bending wire 161*u* and the lower bending wire 161*cd*, or may be performed separately.

The power transmission system optimized by the initialization operation is not limited to the bending wire 160 with slack. The power transmission system optimized by the initialization operation may be a portion where the first coupling portion 156*c* of the attachment/detachment portion 150 and the first coupled portion 256*c* of the drive device 200 are coupled.

According to the electric endoscope system 1000 according to this embodiment, the power transmission system that transmits the power for bending the bending portion 112 can be optimized by performing the initialization operation of the power transmission system. By pulling the tension of a pair of bending wires 160 (the upper bending wire 161*u* and the lower bending wire 161*d*, or the left bending wire 161*l* and the right bending wire 161*r*) in synchronization, the present embodiment has the effect of reducing the amount of bending when the initialization operation is performed. After the initialization operation is completed, the power transmission efficiency of the power transmission system is improved, and the surgeon S can drive the bending portion 112 more accurately. The electric endoscope system 1000 can perform the initialization operation regardless of the bending shape of the insertion portion 110 including the bending portion 112.

The first embodiment of the present invention has been described in detail above with reference to the drawings, but the specific configuration is not limited to this embodiment, and design changes and the like are included within the scope of the present invention. Also, the constituent elements shown in the above-described embodiment and modifications can be combined as appropriate.

Second Embodiment

Figure 20:
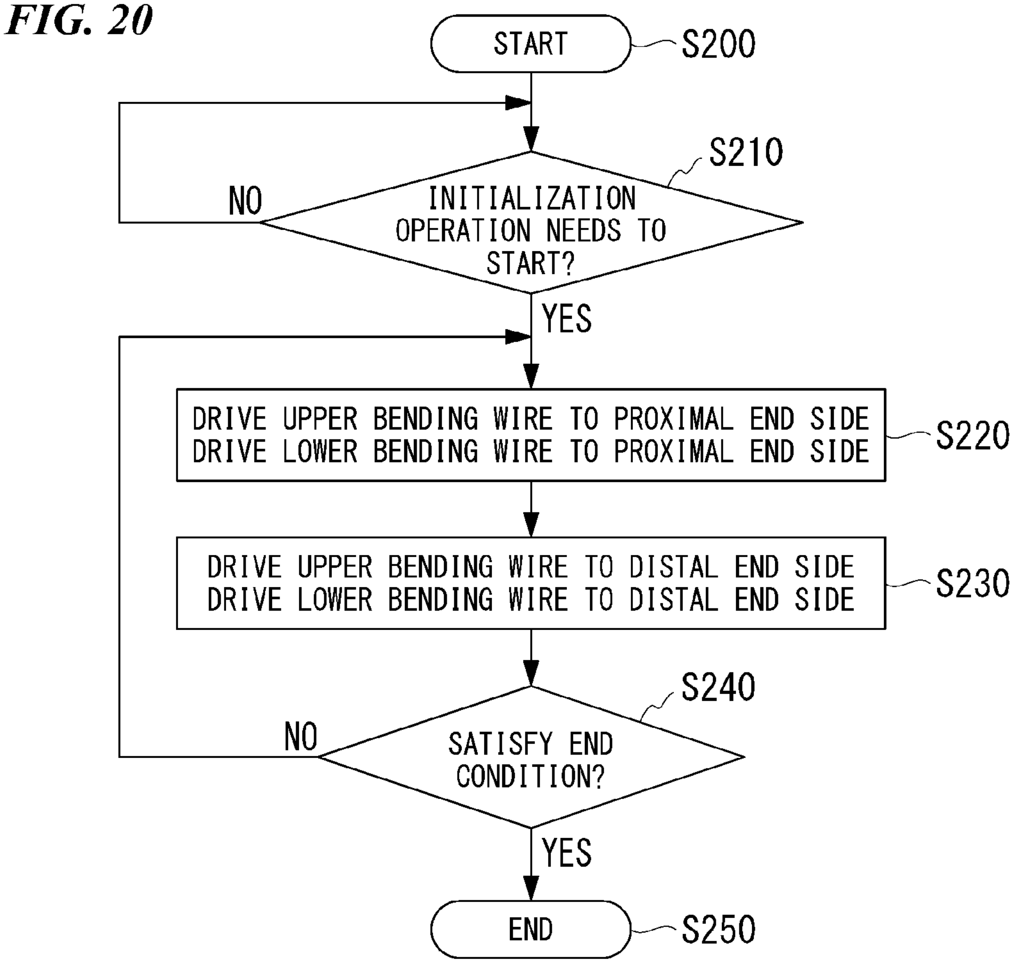
FIG. 20 is a flowchart showing control of the main controller of the electric endoscope system control device according to a second embodiment.

An electric endoscope system 1000B according to a second embodiment of the present invention will be described with reference to FIGS. 20 to 21. In the following description, the same reference numerals are given to the same configurations as those already described, and redundant descriptions will be omitted.

[Electric Endoscope System 1000B]

The electric endoscope system 1000B, as shown in FIG. 1, has the same configuration as the electric endoscope system 1000 of the first embodiment. The electric endoscope system 1000B differs only in operation from the electric endoscope system 1000 of the first embodiment.

Hereinafter, description will be made with reference to the flowchart showing control of the main controller 560 of the control device 600 shown in FIG. 20. When the control device 600 is activated, the main controller 560 starts control after performing initialization (step S200). Next, main controller 560 (mainly the processor 561) executes step S210.

<Step S210: Determining Start of Initialization Operation>

In step S210, the main controller 560 determines whether to start the initialization operation in the same manner as in step S110 of the first embodiment. If the main controller 560 determines that the power transmission system needs to be initialized, then the main controller 560 executes step S220.

<Step S220: First Step of Initialization Operation>

The main controller 560 drives the first motor portion 256*b* to rotate the first shaft 256*a* by controlling the drive controller 260 in step S220. By rotating the first shaft 256*a* clockwise when viewed from the distal end side to the proximal end side, the upper bending wire 161*u* is pulled. As a result, the upper bending wire 161*u* moves to the proximal end side (A2).

In step S220, the main controller 560 controls the drive controller 260 to drive the second motor portion 257*b* to rotate the second shaft 257*a*. By rotating the second shaft 257*a* counterclockwise when viewed from the distal end side to the proximal end side, the lower bending wire 161*d* is pulled. As a result, the lower bending wire 161*d* moves to the proximal end side (A2).

Figure 21:
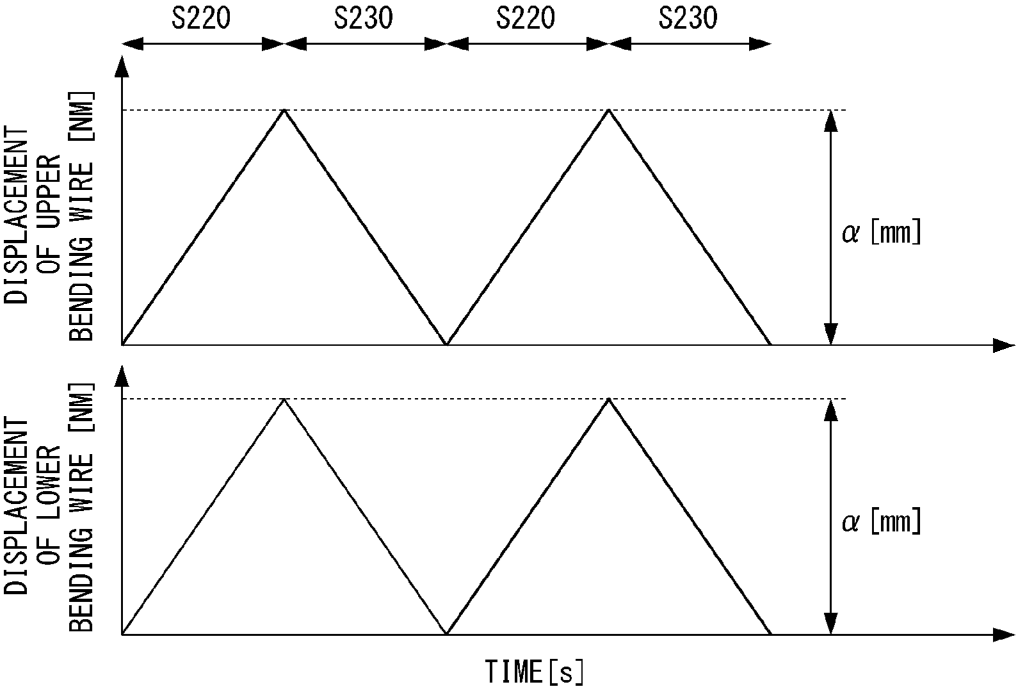
FIG. 21 is a graph showing displacement amounts of an upper bending wire and a lower bending wire.

FIG. 21 is a graph showing displacement amounts of the upper bending wire 161*u* and the lower bending wire 161*d*. The main controller 560 simultaneously drives the upper bending wire 161*u* and the lower bending wire 161*d*. The main controller 560 causes the displacement amount of the upper bending wire 161*u* and the displacement amount of the lower bending wire 161*d* to substantially match. It should be noted that the origin of the graph shown in FIG. 21 is not necessarily the wire pulling amount of 0, but the pulling amount of each wire at the time of execution of the initialization operation.

The main controller 560 drives the upper bending wire 161*u* and the lower bending wire 161*d* at a speed β mm/s to move α mm toward the proximal end side (A2). The main controller 560 determines the movement distance α mm such that the bending amount of the bending portion 112 is within a predetermined range. Specifically, it is thought that a change in the field of view of about 20% can be corrected and treated by a doctor's operation, and the main controller 560 determines the movement distance α mm so that the change in the field of view of the imaging portion 111*c* is 20% or less. More preferably, the moving distance α mm is determined so that the change in the field of view is 15% or less. More preferably, the moving distance α mm is determined so that the change in the field of view is 5% or less. The main controller 560 then executes step S230.

<Step S230: Second Step of Initialization Operation>

The main controller 560 drives the first motor portion 256*b* to rotate the first shaft 256*a* by controlling the drive controller 260 in step S230. By rotating the first shaft 256*a* counterclockwise when viewed from the distal end to the proximal end, the upper bending wire 161*u* is loosened. As a result, the upper bending wire 161*u* moves to the distal end side (A1).

In step S230, the main controller 560 controls the drive controller 260 to drive the second motor portion 257*b* to rotate the second shaft 257*a*. By rotating the second shaft 257*a* clockwise when viewed from the distal end to the proximal end, the lower bending wire 161*d* is loosened. As a result, the lower bending wire 161*d* moves to the distal end side (A1).

As shown in FIG. 21, the main controller 560 simultaneously drives the upper bending wire 161*u* and the lower bending wire 161*d*. The main controller 560 causes the displacement amount of the upper bending wire 161*u* and the displacement amount of the lower bending wire 161*d* to substantially match.

The main controller 560 drives the upper bending wire 161*u* and the lower bending wire 161*d* at a speed of α mm/s to move α mm to the distal end side (A1). The towing speed and towing distance in step S230 are the same as the towing speed and towing distance in step S220. The main controller 560 then executes step S230.

<Step S240: Determination of End of Initialization Operation>

In step S240, the main controller 560 determines the end of the power transmission system initialization operation in the same manner as in step S140 of the first embodiment. When the main controller 560 determines that the state of the power transmission system is sufficiently optimized, it ends the initialization operation of the power transmission system.

Since step S220 and step S230 are alternately performed, the amount of bending of the bending portion 112 after the initialization operation substantially matches the amount of bending of the bending portion 112 before the start of the initialization operation.

According to the electric endoscope system 1000B according to this embodiment, the power transmission system that transmits the power for bending the bending portion 112 can be optimized by performing the initialization operation of the power transmission system. By pulling the tension of a pair of bending wires 160 (the upper bending wire 161*u* and the lower bending wire 161*d*, or the left bending wire 161*l* and the right bending wire 161*r*) in synchronization, the present embodiment has the effect of reducing the amount of bending when the initialization operation is performed. Since the electric endoscope system 1000B can independently pull or loosen a pair of bending wires corresponding to the UD direction and the LR direction, the bending wires 160 can be controlled more accurately in the initialization operation.

As described above, the second embodiment of the present invention has been described in detail with reference to the drawings, but the specific configuration is not limited to this embodiment, and design changes and the like are also included within the scope of the present invention. Also, the constituent elements shown in the above-described embodiment and modifications can be combined as appropriate.

Third Embodiment

Figure 22:
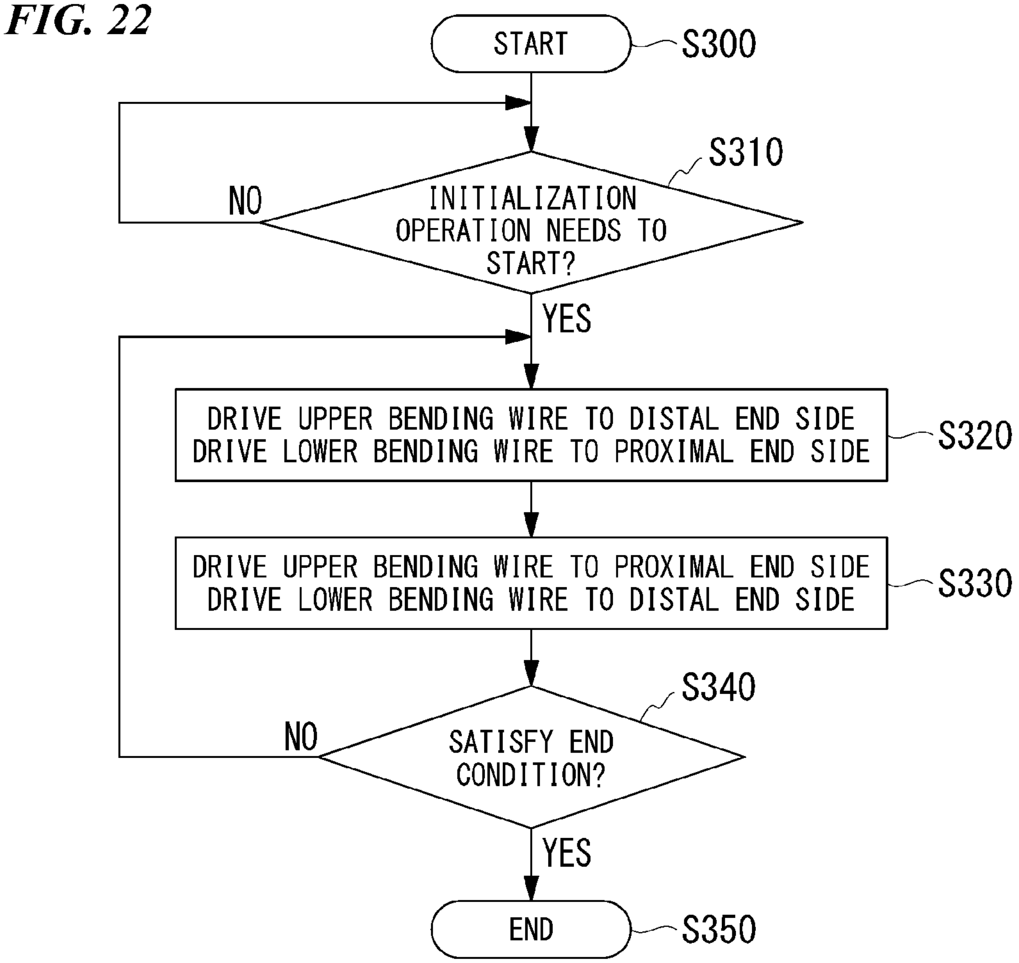
FIG. 22 is a flowchart showing control of the main controller in the control device for the electric endoscope system according to a third embodiment.

An electric endoscope system 1000D according to a third embodiment of the present invention will be described with reference to FIGS. 22 to 23. In the following description, the same reference numerals are given to the same configurations as those already described, and redundant descriptions will be omitted.

[Electric Endoscope System 1000D]

The electric endoscope system 1000D has the same configuration as the electric endoscope system 1000 of the first embodiment, as shown in FIG. 1. The electric endoscope system 1000D differs from the electric endoscope system 1000 of the first embodiment only in operation.

Hereinafter, description will be made with reference to the flowchart showing control of the main controller 560 of the control device 600 shown in FIG. 22. When the control device 600 is activated, the main controller 560 starts control after performing initialization (step S300). Next, main controller 560 (mainly the processor 561) executes step S310.

<Step S310: Determining Start of Initialization Operation>

In step S310, the main controller 560 determines whether to start the initialization operation in the same manner as in step S110 of the first embodiment. When the main controller 560 determines that the power transmission system needs to be initialized, it then executes step S320.

<Step S320: First Step of Initialization Operation>

The main controller 560 drives the first motor portion 256*b* to rotate the first shaft 256*a* by controlling the drive controller 260 in step S320. By rotating the first shaft 256*a* counterclockwise when viewed from the distal end to the proximal end, the upper bending wire 161*u* is loosened. As a result, the upper bending wire 161*u* moves to the distal end side (A1).

In step S320, the main controller 560 controls the drive controller 260 to drive the second motor portion 257*b* to rotate the second shaft 257*a*. By rotating the second shaft 257*a* counterclockwise when viewed from the distal end side to the proximal end side, the lower bending wire 161*d* is pulled. As a result, the lower bending wire 161*d* moves to the proximal end side (A2).

Figure 23:
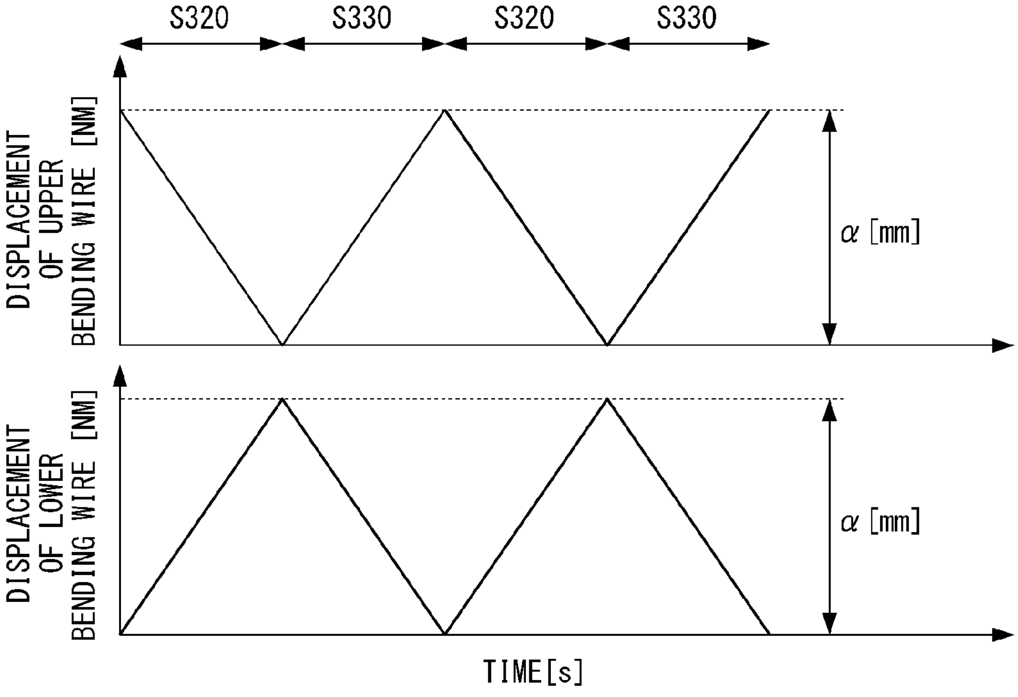
FIG. 23 is a graph showing the amount of displacement of the bending wire controlled by the main controller.

FIG. 23 is a graph showing displacement amounts of the upper bending wire 161*u* and the lower bending wire 161*d*. The main controller 560 simultaneously drives the upper bending wire 161*u* and the lower bending wire 161*d*. The main controller 560 substantially matches the absolute value of the displacement amount of the upper bending wire 161*u* and the absolute value of the displacement amount of the lower bending wire 161*d*. The origin of the graph shown in FIG. 23 is not necessarily the wire pulling amount of 0, but the pulling amount of each wire at the time of execution of the initialization operation.

The main controller 560 drives the upper bending wire 161*u* at a speed β mm/s to move it to the distal end side (A1) by α mm. The main controller 560 drives the lower bending wire 161*d* at a speed of β mm/s to move it to the proximal end side (A2) by α mm. The main controller 560 determines the movement distance α mm such that the bending amount of the bending portion 112 is within a predetermined range. Specifically, it is thought that a change in the field of view of about 20% can be corrected and treated by a doctor's operation, and the main controller 560 determines the movement distance α mm so that the change in the field of view of the imaging portion 111*c* is 20% or less. More preferably, the moving distance α mm is determined so that the change in the field of view is 15% or less. More preferably, the moving distance α mm is determined so that the change in the field of view is 5% or less. The main controller 560 then executes step S330.

<Step S330: Second Step of Initialization Operation>

The main controller 560 drives the first motor portion 256*b* to rotate the first shaft 256*a* by controlling the drive controller 260 in step S330. By rotating the first shaft 256*a* clockwise when viewed from the distal end side to the proximal end side, the upper bending wire 161*u* is pulled. As a result, the upper bending wire 161*u* moves to the proximal end side (A2).

In step S320, the main controller 560 controls the drive controller 260 to drive the second motor portion 257*b* to rotate the second shaft 257*a*. By rotating the second shaft 257*a* clockwise when viewed from the distal end to the proximal end, the lower bending wire 161*d* is loosened. As a result, the lower bending wire 161*d* moves to the distal end side (A1).

As shown in FIG. 23, the main controller 56) simultaneously drives the upper bending wire 161*u* and the lower bending wire 161*d*. The main controller 560 substantially matches the absolute value of the displacement amount of the upper bending wire 161*u* and the absolute value of the displacement amount of the lower bending wire 161*d*.

The main controller 560 drives the upper bending wire 161*u* at a speed β mm/s to move it to the proximal end side (A2) by α mm. The main controller 560 drives the lower bending wire 161*d* at a speed of β mm/s to move it to the distal end side (A1) by α mm. The towing speed and towing distance in step S330 are the same as the towing speed and towing distance in step S320. The main controller 560 then executes step S330.

<Step S340: Determination of End of Initialization Operation>

In step S340, the main controller 560 determines the end of the power transmission system initialization operation in the same manner as in step S140 of the first embodiment. When the main controller 560 determines that the state of the power transmission system is sufficiently optimized, it ends the initialization operation of the power transmission system.

Since step S320 and step S330 are alternately performed, the amount of bending of the bending portion 112 after the initialization operation substantially matches the amount of bending of the bending portion 112 before the start of the initialization operation.

According to the electric endoscope system 1000D according to this embodiment, the power transmission system that transmits the power for bending the bending portion 112 can be optimized by performing the initialization operation of the power transmission system. Since the electric endoscope system 1000D can independently pull or loosen a pair of bending wires corresponding to the UD direction and the LR direction, the bending wires 160 can be controlled more accurately in the initialization operation.

As described above, the third embodiment of the present invention has been described in detail with reference to the drawings, but the specific configuration is not limited to this embodiment, and design changes and the like are included within the scope of the present invention. Also, the constituent elements shown in the above-described embodiment and modifications can be combined as appropriate.

Fourth Embodiment

Figure 24:
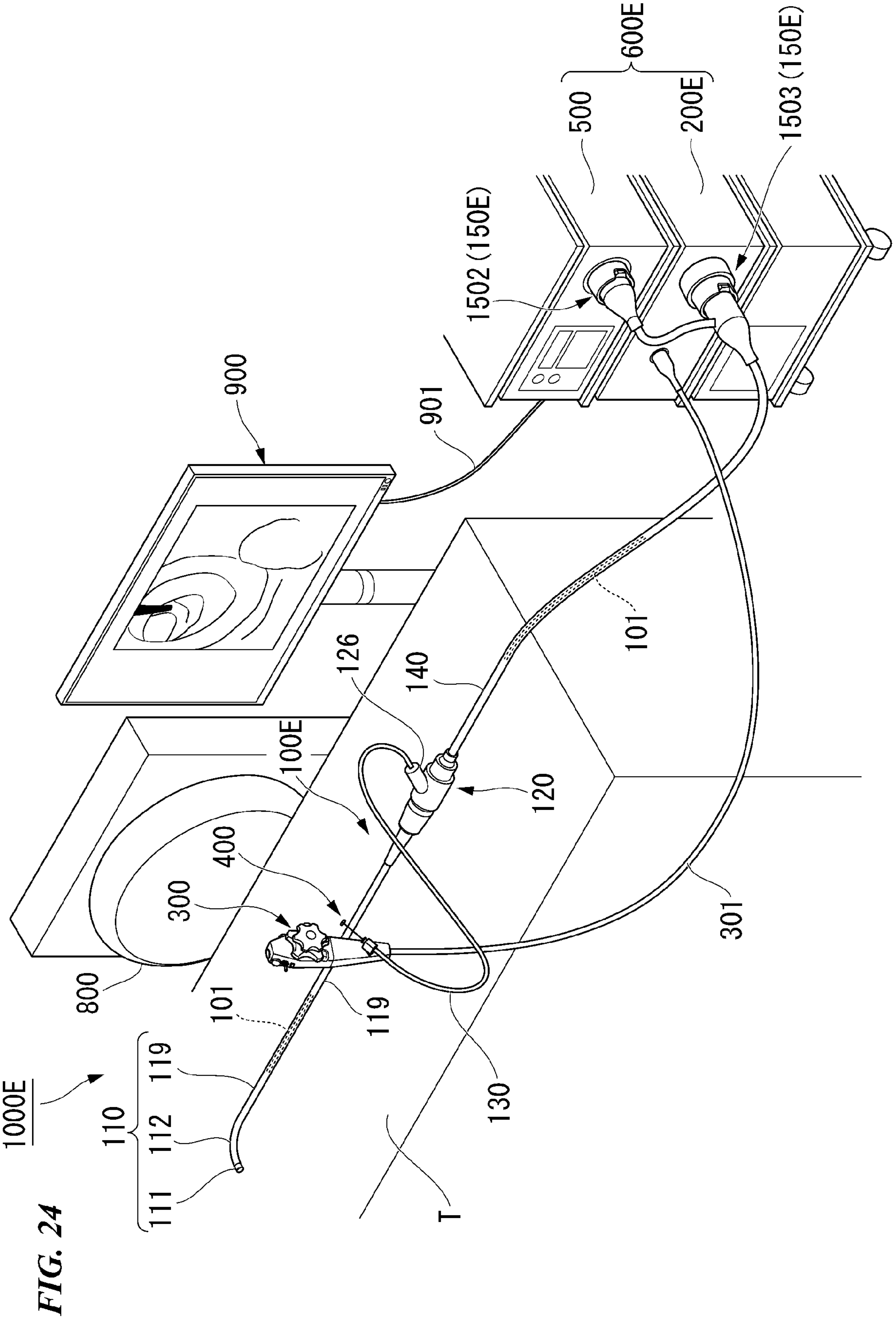
FIG. 24 is an overall view of an electric endoscope system according to a fourth embodiment.

An electric endoscope system 1000E according to a fourth embodiment of the present invention will be described with reference to FIGS. 24 to 29. In the following description, the same reference numerals are given to the same configurations as those already described, and redundant descriptions will be omitted. FIG. 24 is an overall view of an electric endoscope system 1000E according to this embodiment.

[Electric Endoscope System 1000]

The electric endoscope system 1000E is a medical system for observing and treating the inside of the patient P lying on the operation table T, as shown in FIG. 24. The electric endoscope system 1000E includes an endoscope 100E, a drive device 200E, an operation device 300, a treatment tool 400, an image control device 500, an observation device 800, and a display device 900. The drive device 200E and the image control device 500 constitute a control device 600E that controls the electric endoscope system 1000E.

[Endoscope 100E]

The endoscope 100E includes the insertion portion 110, the connecting portion 120, the extracorporeal flexible portion 140, an attachment/detachment portion 150E, the bending wire 160, and the internal object 170. The insertion portion 110, the connecting portion 120, the extracorporeal flexible portion 140, and the attachment/detachment portion 150E are connected in order from the distal end side.

[Attachment/Detachment Portion 150E]

The attachment/detachment portion 150E includes a first attachment/detachment portion 1503 attached to the drive device 200E and the second attachment/detachment portion 1502 attached to the video control device 500, as shown in FIG. 24. The first attachment/detachment portion 1503 and the second attachment/detachment portion 1502 may be an integral attachment/detachment portion.

The internal path 101 formed inside the extracorporeal flexible portion 140 branches into the first attachment/detachment portion 1503 and the second attachment/detachment portion 1502. The bending wire 160 and the air supply/suction tube 172 are inserted through the first attachment/detachment portion 1503. The imaging cable 173 and the light guide 174 are inserted through the second attachment/detachment portion 1502.

Figure 25:
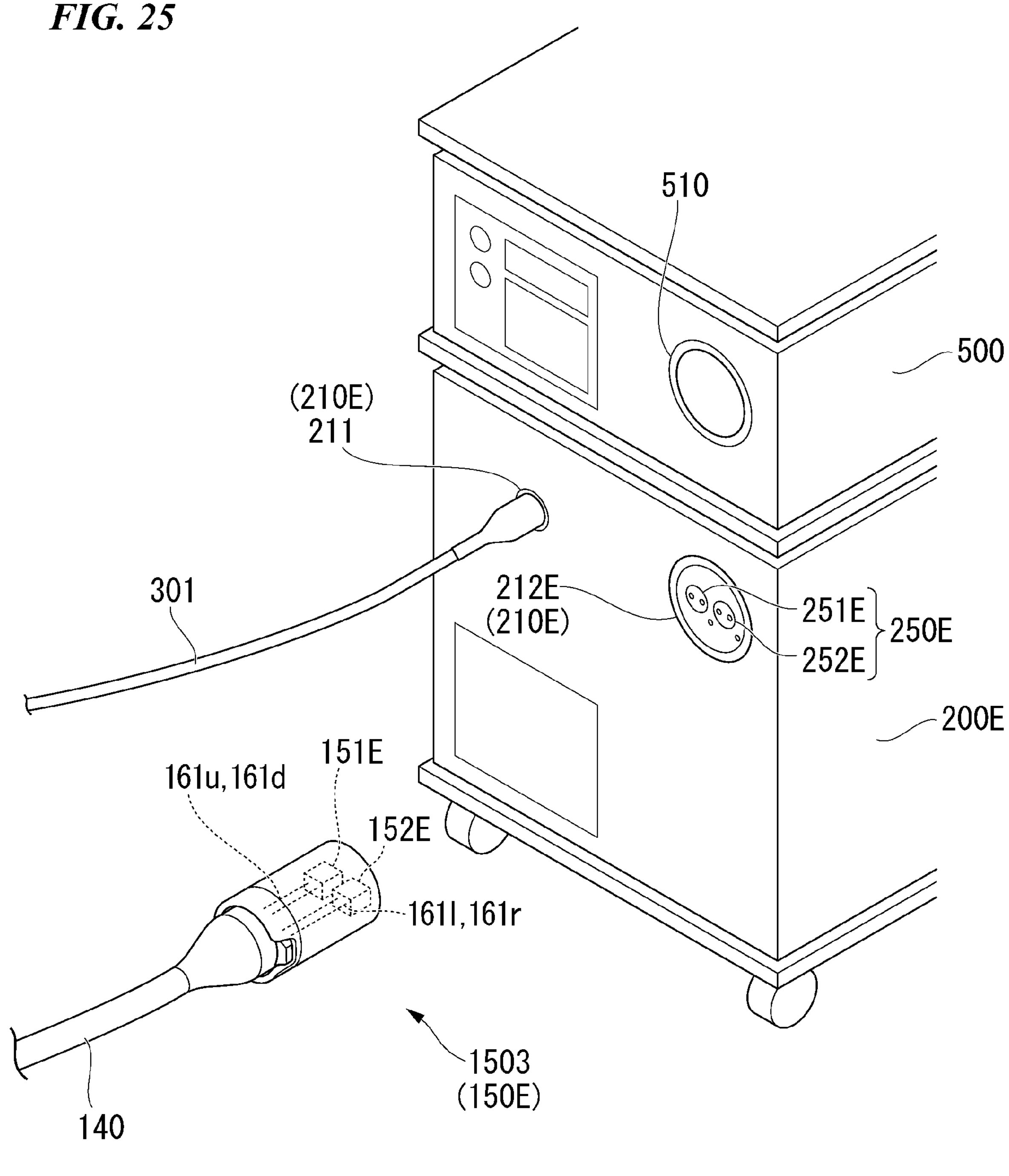
FIG. 25 is a diagram showing the first attachment/detachment portion before attachment to the drive device of the electric endoscope system.

FIG. 25 is a diagram showing the first attachment/detachment portion 1503 before being attached to the drive device 200E.

The first attachment/detachment portion 1503 has a vertical bending wire attachment/detachment portion 151E and a horizontal bending wire attachment/detachment portion 152E.

The vertical bending wire attachment/detachment portion 151E is a mechanism that detachably connects wires (the upper bending wire 161*u* and the lower bending wire 161*d*) for bending the bending portion 112 in the UD direction to the drive device 200E.

The horizontal bending wire attachment/detachment portion 152E is a mechanism that detachably connects the wires (the left bending wire 161*l* and the right bending wire 161*r*) for bending the bending portion 112 in the LR direction to the drive device 200E.

The horizontal bending wire attachment/detachment portion 152E has the same structure as the vertical bending wire attachment/detachment portion 151E, so illustration and description thereof are omitted.

Figure 26:
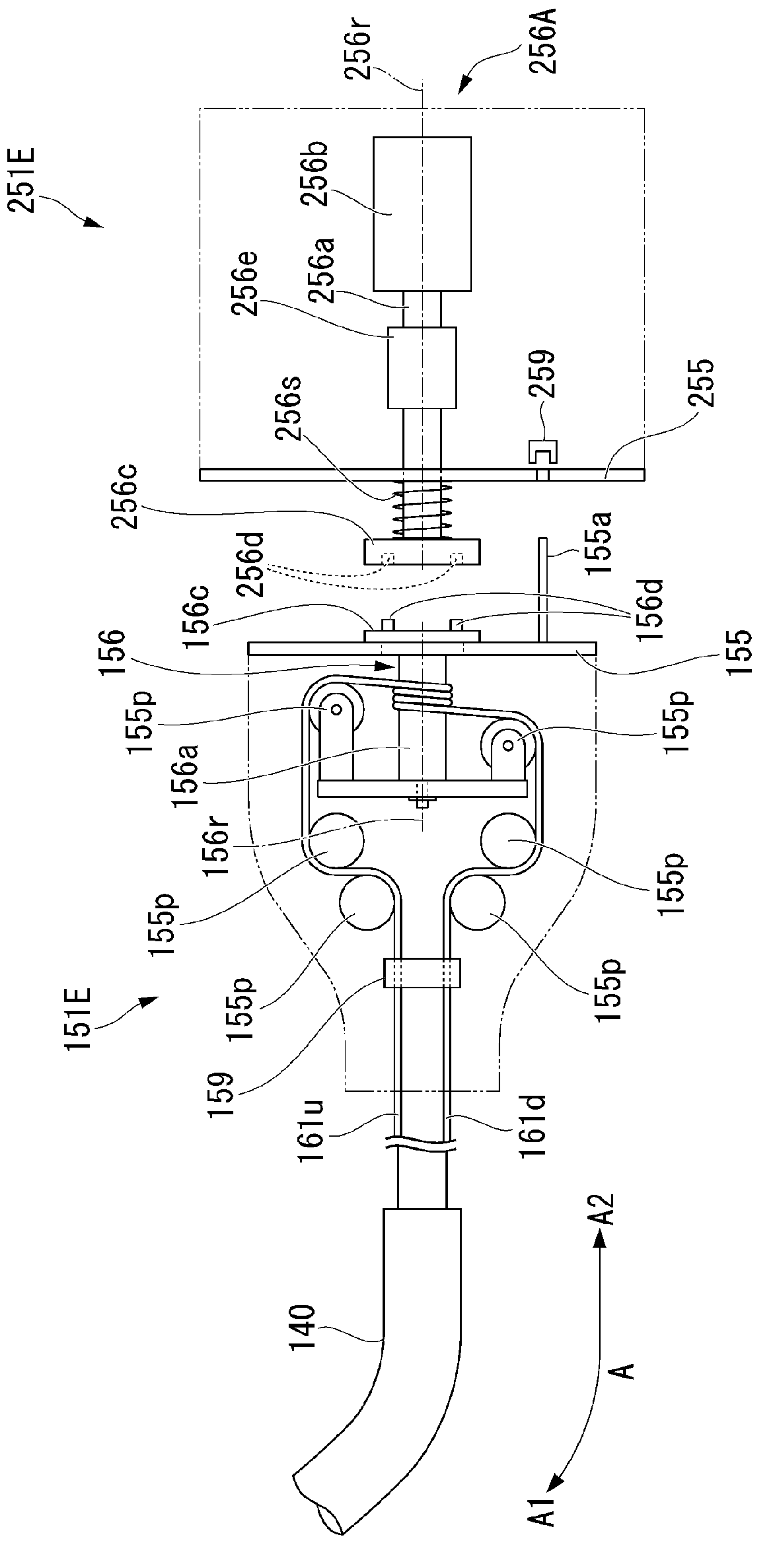
FIG. 26 is a view showing the first vertical bending wire attachment/detachment portion before attachment to the drive device.
Figure 27:
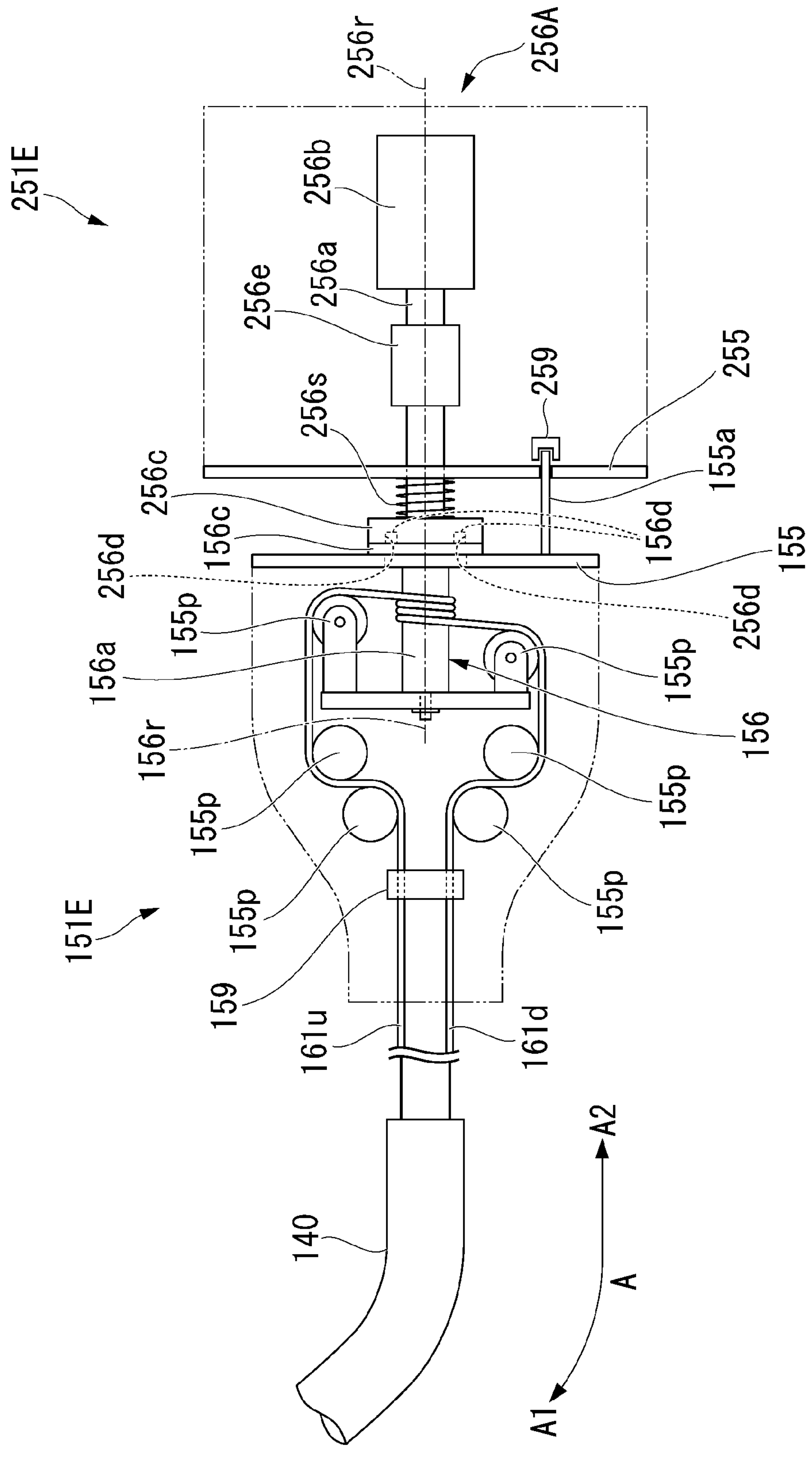
FIG. 27 is a diagram showing the first vertical bending wire attachment/detachment portion attached to the drive device.

FIG. 26 is a diagram showing the vertical bending wire attachment/detachment portion 151E before being attached to the drive device 200E. FIG. 27 is a diagram showing the vertical bending wire attachment/detachment portion 151E attached to the drive device 200E. The vertical bending wire attachment/detachment portion 151E has the support member 155, the rotating drum 156, and the tension sensor 159.

The support member 155 supports the rotating drum 156 so that it can advance and retract in the longitudinal direction A. The support member 155 has the attachment/detachment detection dog 155*a* exposed on the proximal end side of the vertical bending wire attachment/detachment portion 151E, and the plurality of bend pulleys 155*p*.

The bend pulley 155*p* changes the conveying direction of the upper bending wire 161*u* inserted through the extracorporeal flexible portion 140 and guides the upper bending wire 161*u* to the rotating drum 156. The bend pulley 155*p* changes the conveying direction of the lower bending wire 161*d* inserted through the extracorporeal flexible portion 140 and guides the lower bending wire 161*d* to the rotating drum 156.

The rotating drum 156 is supported by the supporting member 155 so as to be rotatable around the drum rotating shaft 156*r* extending along the longitudinal direction A. The rotating drum 156 has the winding pulley 156*a* and the coupling portion 156*c*.

The winding pulley 156*a* pulls or feeds the upper bending wire 161*u* and the lower bending wire 161*d* by rotating around the drum rotation shaft 156*r*. As the winding pulley 156*a* rotates clockwise when viewed from the distal end side to the proximal end side, the upper bending wire 161*u* is wound around the winding pulley 156*a* and pulled, and the lower bending wire 161*d* is sent out from the winding pulley 156*a*. Conversely, when the winding pulley 156*a* rotates counterclockwise, the upper bending wire 161*u* is sent out from the winding pulley 156*a*, and the lower bending wire 161*d* is wound around the winding pulley 156*a* and pulled.

The coupling portion 156*c* is a disk member that rotates about the drum rotation shaft 156*r*. The coupling portion 156*c* is fixed to the proximal end of the winding pulley 156*a* and rotates together with the winding pulley 156*a*. The coupling portion 156*c* is exposed on the proximal end side of the vertical bending wire attachment/detachment portion 151E. The two fitting protrusions 156*d* are formed on the proximal end side surface of the coupling portion 156*c*. The two fitting protrusions 156*d* are formed on both sides of the drum rotating shaft 156*r*.

The tension sensor 159 detects the tension of the upper bending wire 161*u* and the lower bending wire 161*d*. The detection result of tension sensor 159 is acquired by a drive controller 260E.

[Drive Device 200E]

Figure 28:
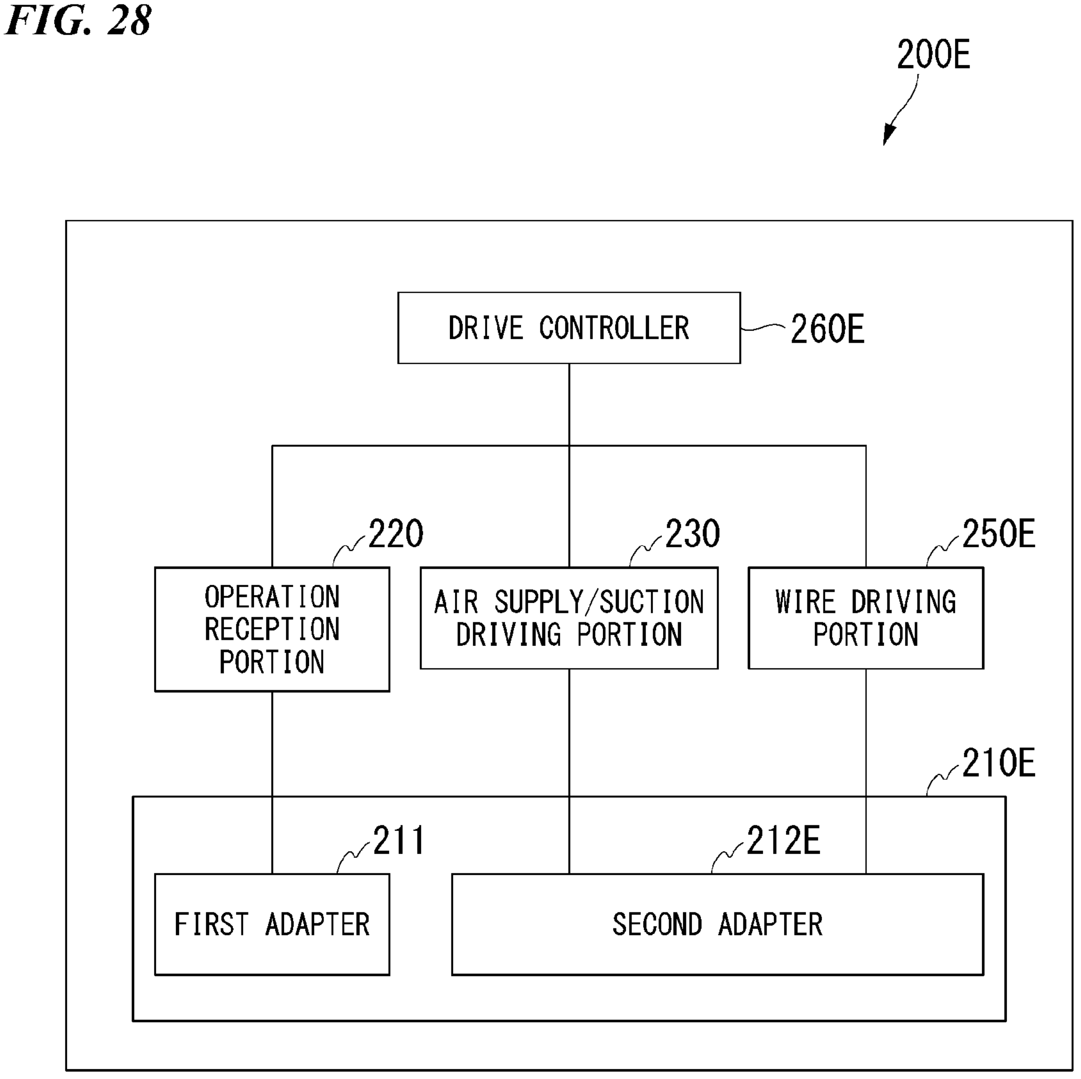
FIG. 28 is a functional block diagram of the drive device.

FIG. 28 is a functional block diagram of the drive device 200E.

The drive device 200E includes an adapter 210E, the operation reception portion 220, the air supply/suction driving portion 230, a wire driving portion 250E, and the drive controller 260E.

The adapter 210E, as shown in FIG. 25, has the first adapter 211 and a second adapter 212E. The first adapter 211 is an adapter to which the operation cable 301 is detachably connected. The second adapter 212E is an adapter to which the first attachment/detachment portion 1503 of the endoscope 100 is detachably connected.

The wire driving portion 250E drives the bending wire 160 by coupling with the vertical bending wire attachment/detachment portion 151E and the horizontal bending wire attachment/detachment portion 152E.

As shown in FIG. 25, the wire driving portion 250E has a vertical bending wire driving portion 251E and a horizontal bending wire driving portion 252E.

The vertical bending wire driving portion 251E is a mechanism that is coupled with the vertical bending wire attachment/detachment portion 151E to drive the wires (the upper bending wire 161*u* and the lower bending wire 161*d*) that bend the bending portion 112 in the UD direction.

The vertical bending wire driving portion 252E is a mechanism that is coupled with the horizontal bending wire attachment/detachment portion 152E to drive the wires (the left bending wire 161*l* and the right bending wire 161*r*) that bend the bending portion 112 in the LR direction.

The vertical bending wire driving portion 252E has the same structure as the vertical bending wire driving portion 251E, so illustration and description thereof will be omitted.

The vertical bending wire driving portion 251E has the support member 255, a bending wire driving portion 256A, an engaging member 258, and the attachment/detachment sensor 259, as shown in FIG. 26.

The bending wire driving portion 256A is coupled with the rotary drum 156 of the vertical bending wire attachment/detachment portion 151E to drive the upper bending wire 161*u* and the lower bending wire 161*d*. The bending wire driving portion 256A has the shaft 256*a*, the motor portion 256*b*, the coupled portion 256*c*, the torque sensor 256*e*, and the elastic member 256*s*.

The shaft 256*a* is supported by the support member 255 so as to be rotatable around the shaft rotation axis 256*r* and to be advanced and retracted in the longitudinal direction A. When the first attachment/detachment portion 1503 of the endoscope 100 is attached to the drive device 200E, the shaft rotation axis 256*r* coincides with the drum rotation axis 156*r*.

The motor portion 256*b* has a motor such as a DC motor, a motor driver that drives the motor, and a motor encoder. The motor rotates the shaft 256*a* around the shaft rotation axis 256*r*. The motor driver is controlled by the drive controller 260E.

The coupled portion 256*c* is a disc member that rotates around the shaft rotation axis 256*r*. The coupled portion 256*c* is fixed to the distal end of the shaft 256*a* and rotates integrally with the shaft 256*a*. As shown in FIG. 26, the coupled portion 256*c* is exposed at the distal end side of the vertical bending wire driving portion 251. Two fitting recesses 256*d* are formed on the front end side surface of the coupled portion 256*c*. The two fitting recesses 256*d* are formed on both sides of the shaft rotation axis 256*r*.

As shown in FIG. 27, the fitting protrusions 156*d* and the fitting recesses 256*d* are fitted to couple the coupling portion 156*c* and the coupled portion 256*c*. As a result, the rotation of the shaft 256*a* by the motor portion 256*b* is transmitted to the rotating drum 156. As the shaft 256*a* rotates clockwise when viewed from the distal end side to the proximal end side, the upper bending wire 161*u* is pulled and the lower bending wire 161*d* is sent out. Conversely, by rotating the shaft 256*a* counterclockwise, the upper bending wire 161*u* is delivered and the lower bending wire 161*d* is pulled.

The torque sensor 256*e* detects the rotational torque of the shaft 256*a* about the shaft rotation axis 256*r*. The detection result of the torque sensor 256*e* is acquired by the drive controller 260E.

The elastic member 256*s* is, for example, a compression spring, and has a distal end in contact with the coupled portion 256*c* and a proximal end in contact with the support member 255. The elastic member 256*s* urges the coupled portion 256*c* toward the distal end side (A1). As shown in FIG. 27, when the coupling portion 156*c* is attached, the coupled portion 256*c* moves toward the proximal end side (A2) together with the shaft 256*a*.

As shown in FIG. 27, the attachment/detachment sensor 259 detects attachment/detachment of the vertical bending wire attachment/detachment portion 151E to/from the vertical bending wire driving portion 251 by detecting engagement and disengagement with the attachment/detachment detection dog 155*a*. The detection result of the attachment/detachment sensor 259 is acquired by the drive controller 260E.

The drive controller 260E controls the entire drive device 200E. The drive controller 260E acquires the operation input received by the operation reception portion 220. The drive controller 260E controls the air supply/suction driving portion 230 and the wire driving portion 250E based on the acquired operation input. The drive controller 260E may perform other processing such as image processing and image recognition processing.

The drive controller 260E is a program-executable computer that includes a processor, a memory, a storage portion capable of storing programs and data, and an input/output control portion. The functions of the drive controller 260E are implemented by the processor executing a program. At least some of the functions of drive controller 260E may be realized by a dedicated logic circuit.

The drive controller 260E desirably has high computational performance in order to control the plurality of motors that drive the plurality of bending wires 160 with high accuracy.

It should be noted that the drive controller 260E may further have a configuration other than the processor, memory, storage portion, and input/output control portion. For example, the drive controller 260E may further include an image calculation portion that performs some or all of the image processing and image recognition processing. By further including an image calculation portion, the drive controller 260E can execute specific image processing and image recognition processing at high speed. The image calculation portion may be mounted in a separate hardware device connected via a communication line.

[Operation of the Electric Endoscope System 1000E]

Next, the operation of the electric endoscope system 1000E of this embodiment will be described. Specifically, a procedure for observing and treating an affected area formed on the wall of the large intestine using the electric endoscope system 1000E will be described.

Figure 29:
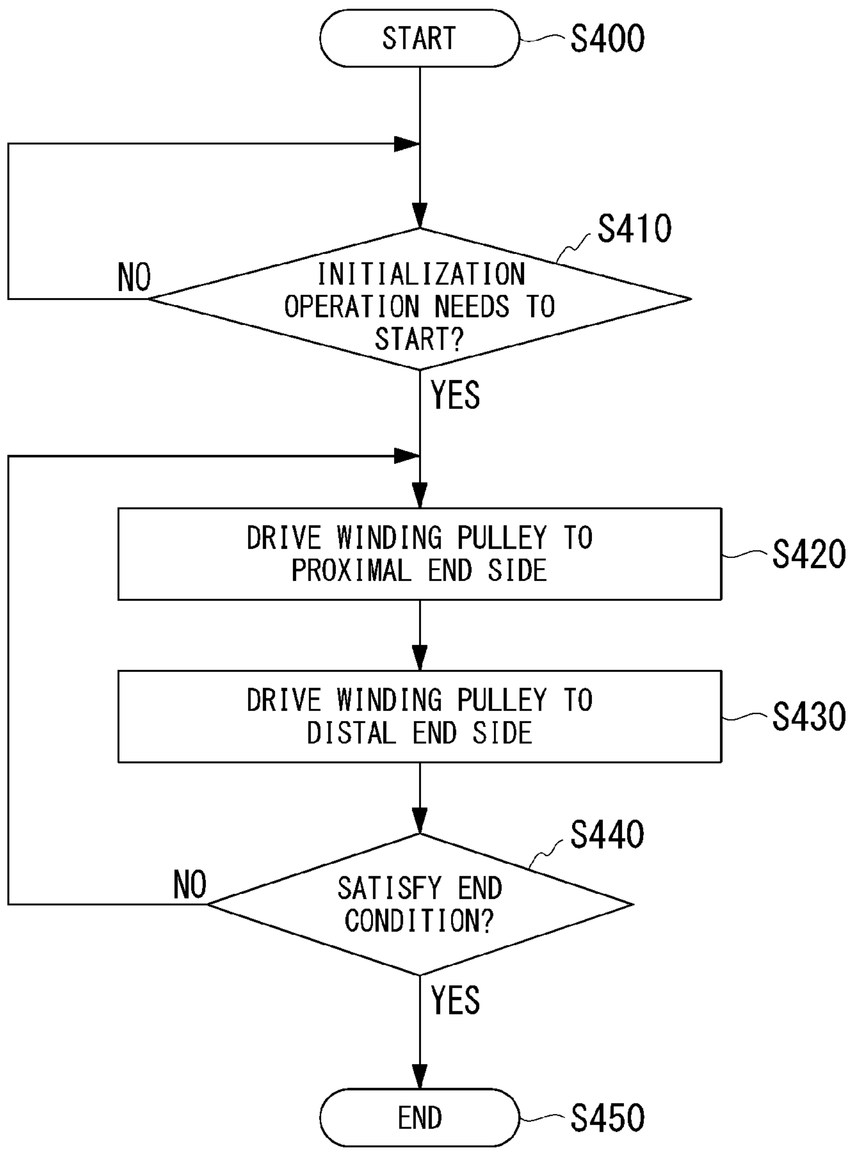
FIG. 29 is a flowchart showing control of the main controller of the drive device.

Hereinafter, description will be made with reference to the flowchart showing control of the main controller 560 of the control device 600E shown in FIG. 29. When the control device 600E is activated, the main controller 560 starts control after performing initialization (step S400). Next, main controller 560 (mainly the processor 561) executes step S410.

<Step S410: Determining Start of Initialization Operation>

In step S410, the main controller 560 determines whether to start the initialization operation in the same manner as in step S110 of the first embodiment. When the main controller

560 determines that the initialization operation of the power transmission system is necessary, then the main controller 560 executes step S420.

<Step S420: First Step of Initialization Operation>

In step S420, the main controller 560 drives the bending wire driving portion 256A of the drive device 200E by controlling the drive controller 260E to move the rotating drum 156 of the attachment/detachment portion 150E to the proximal end side (A2) in the longitudinal direction A. The winding pulley 156*a* moves to the proximal end side (A2) along the drum rotating shaft 156*r*. As a result, the upper bending wire 161*u* and the lower bending wire 161*d* move to the proximal end side (A2).

The main controller 560 drives the upper bending wire 161*u* and the lower bending wire 161*d* at a speed β mm/s to move it toward the proximal end side (A2) by α mm. The main controller 560 determines the movement distance α mm such that the bending amount of the bending portion 112 is within a predetermined range. Specifically, if the change in field of view is a deviation of about 20%, it can be corrected by a doctor's operation and treated, and the main controller 560 determines the movement distance α mm so that the change in the field of view of the imaging portion 111*c* is 20% or less. More preferably, the moving distance α mm is determined so that the change in the field of view is 15% or less. More preferably, the moving distance α mm is determined so that the change in the field of view is 5% or less. The main controller 560 then executes step S430.

<Step S430: Second Step of Initialization Operation>

In step S430, the main controller 560 controls the drive controller 260E to drive the bending wire driving portion 256A of the drive device 200E to move the rotating drum 156 of the attachment/detachment portion 150E to the distal end side (A1) in the longitudinal direction A. The winding pulley 156*a* moves toward the distal end side (A1) along the drum rotation shaft 156*r*. As a result, the upper bending wire 161*u* and the lower bending wire 161*d* move to the distal end side (A1).

The main controller 560 drives the upper bending wire 161*u* and the lower bending wire 161*d* at a speed of β mm/s to move α mm to the distal end side (A1). The towing speed and towing distance in step S430 are the same as the towing speed and towing distance in step S420. The main controller 560 then executes step S440.

<Step S440: Determination of End of Initialization Operation>

At step S440, the main controller 560 determines whether the initialization operation of the power transmission system is finished, similar to step S140 of the first embodiment. When the main controller 560 determines that the state of the power transmission system is sufficiently optimized, it ends the initialization operation of the power transmission system.

Since step S420 and step S430 are alternately performed, the amount of bending of the bending portion 112 after the initialization operation substantially matches the amount of bending of the bending portion 112 before the start of the initialization operation.

According to the electric endoscope system 1000E according to this embodiment, the power transmission system that transmits the power for bending the bending portion 112 can be optimized by performing the initialization operation of the power transmission system. Since the electric endoscope system 1000E can independently pull or loosen a pair of bending wires corresponding to the UD direction and the LR direction, the bending wires 160 can be controlled more accurately in the initialization operation.

As described above, the fourth embodiment of the present invention has been described in detail with reference to the drawings, but the specific configuration is not limited to this embodiment, and design changes and the like are included within the scope of the present invention. Also, the constituent elements shown in the above-described embodiment and modifications can be combined as appropriate.

(Modification)

For example, in the above embodiment, the bending wire 160 is wound around the winding pulley, and the bending wire 160 is pulled and loosened by rotating the winding pulley. However, the driving method of the bending wire 160 is not limited to this, and may be another method using a driving portion such as an electric actuator.

The program in each embodiment may be recorded in a computer-readable recording medium, and the program recorded in this recording medium may be read into a computer system and executed. The "computer system" includes hardware such as an OS and peripheral devices. The term "computer-readable recording medium" refers to portable media such as flexible discs, magneto-optical discs, ROMs and CD-ROMs, and storage devices such as hard discs incorporated in computer systems. Furthermore, "computer-readable recording medium" refers to a program that dynamically retains programs for a short period of time, like a communication line when transmitting a program via a network such as the Internet or a communication line such as a telephone line. It may also include something that holds the program for a certain period of time, such as a volatile memory inside a computer system that serves as a server or client in that case. Further, the program may be for realizing some of the functions described above, or may be capable of realizing the functions described above in combination with a program already recorded in the computer system.

INDUSTRIAL APPLICABILITY

The present invention can be applied to medical systems for observing and treating the inside of hollow organs.

What is claimed is:

1. A manipulator system comprising:

a manipulator comprising:
- a bending portion;
- a first bending wire configured to bend the bending portion in a first direction; and
- a second bending wire configured to bend the bending portion in a second direction opposite the first direction;

a driving portion configured to pull and loosen the first bending wire and the second bending wire; and a control device configured to control the driving portion to perform an initialization operation, the initialization operation comprising alternately performing:
- a first step of pulling the first bending wire and pulling the second bending wire, while substantially matching an amount of change in a tension of the first bending wire and an amount of change in a tension of the second bending wire; and
- a second step of loosening the first bending wire and loosening the second bending wire, while substantially matching an amount of change in a tension of the first bending wire and an amount of change in a tension of the second bending wire.

2. The manipulator system according to claim 1, wherein:

the driving portion comprises a first pulley around which the first bending wire is wound, and a second pulley around which the second bending wire is wound, and the control device is configured to control the driving portion to perform the initialization operation by rotating the first pulley and the second pulley.

3. The manipulator system according to claim 1, wherein:
the manipulator further comprises an insertion portion comprising the bending portion, and
the control device is configured to:
acquire a shape of the insertion portion;
determine whether an amount of change in the shape of the insertion portion is equal to or greater than a predetermined amount; and
control the driving portion to start the initialization operation in response to determining that the amount of change in the shape of the insertion portion is equal to or greater than the predetermined amount.

4. The manipulator system according to claim 1, wherein;
the manipulator has an internal path through which a treatment tool can be inserted,
the manipulator further comprises a treatment tool sensor configured to detect that the treatment tool has been inserted through the internal path, and
the control device is configured to control the driving portion to start performing the initialization operation in response to the treatment tool sensor detecting the treatment tool.

5. The manipulator system according to claim 1, wherein the control device is configured to:
determine whether the first step and the second step have been performed a predetermined number of times; and
control the driving portion to terminate the initialization operation in response to determining that the first step and the second step have been performed the predetermined number of times.

6. The manipulator system according to claim 1, wherein:
the manipulator further comprises:
a tension sensor configured to detect a tension of the first bending wire and the second bending wire; and
an encoder configured to detect an amount of pulling of the first bending wire and the second bending wire, and
the control device is configured to control the driving portion to terminate the initialization operation based on the tension and the amount of pulling of the first bending wire and the second bending wire.

7. The manipulator system according to claim 1,
wherein the control device is configured to control the driving portion to perform the initialization operation so that an amount of change in a bending shape of the bending portion when the initialization operation ended compared to when the initialization operation is started falls within a predetermined range.

8. The manipulator system according to claim 7, wherein:
the manipulator further comprises an imaging portion provided on a distal end side of the bending portion, and
the predetermined range is a range in which a change in a field of view imaged by the imaging portion falls within a change-in-a-field-of-view predetermined range.

9. The manipulator system according to claim 8, wherein the change-in-a-field-of-view predetermined range is 20% or less.

10. A method for operating a manipulator having a bending portion, a first bending wire configured to bend the bending portion in a first direction; and a second bending wire configured to bend the bending portion in a second direction opposite the first direction, the method comprising:
controlling a driving portion to perform an initialization operation, the initialization operation comprising alternately performing:
a first step of pulling the first bending wire and pulling the second bending wire, while substantially matching an amount of change in a tension of the first bending wire and an amount of change in a tension of the second bending wire; and
a second step of loosening the first bending wire and loosening the second bending wire, while substantially matching an amount of change in a tension of the first bending wire and an amount of change in a tension of the second bending wire.

11. The method according to claim 10, wherein:
the manipulator has an internal path through which a treatment tool can be inserted,
the manipulator further comprises a treatment tool sensor configured to detect that the treatment tool has been inserted though the internal path,
the method is configured to control the driving portion to start performing the initialization operation in response to the treatment tool sensor detecting the treatment tool.

12. The method according to claim 10, further comprising:
determining whether the first step and the second step have been performed a predetermined number of times; and
controlling the driving portion to terminate the initialization operation in response to determining that the first step and the second step have been performed the predetermined number of times.

13. The method according to claim 10, wherein:
the manipulator further comprises:
a tension sensor configured to detect a tension of the first bending wire and the second bending wire; and
an encoder configured to detect an amount of pulling of the first bending wire and the second bending wire, and
the method further comprises controlling the driving portion to terminate the initialization operation based on the tension and the amount of pulling of the first bending wire and the second bending wire.

14. The method according to claim 10, comprising:
controlling the driving portion to perform the initialization operation so that an amount of change in a bending shape of the bending portion when the initialization operation ended compared to when the initialization operation is started falls within a predetermined range.

15. The method according to claim 14, wherein:
the manipulator further comprises an imaging portion provided on a distal end side of the bending portion, and
the predetermined range is a range in which a change in a field of view imaged by the imaging portion falls within a change-in-a-field-of-view predetermined range.

16. The method according to claim 15, wherein the change-in-a-field-of-view predetermined range is 20% or less.

17. A manipulator system comprising:
a control device configured to control a driving portion to perform an initialization operation, the initialization operation comprising alternately performing:
a first step of pulling a first bending wire configured to bend a bending portion of a manipulator in a first direction and pulling a second bending wire configured to bend the bending portion in a second direction opposite the first direction, while substantially matching an amount of change in a tension of the first bending wire and an amount of change in a tension of the second bending wire; and a second step of loosening the first bending wire and loosening the second bending wire, while substantially matching an amount of change in a tension of the first bending wire and an amount of change in a tension of the second bending wire.

* * * * *